US012582695B2

(12) United States Patent
Kaminska-Kaczmarek et al.

(10) Patent No.: US 12,582,695 B2
(45) Date of Patent: Mar. 24, 2026

(54) COMPOSITIONS AND METHODS FOR TREATING GLIOMA

(71) Applicant: Instytut Biologii Doświadczalnej im. Marcelego Nenckiego Polska Akademia Nauk, Warsaw (PL)

(72) Inventors: Bozena Kaminska-Kaczmarek, Komorow (PL); Aleksandra Ellert-Miklaszewska, Komorow (PL); Katarzyna Poleszak, Warsaw (PL); Maria Pasierbinska, Pruszkow (PL); Pawel Wisniewski, Blizne Jasinskiego (PL)

(73) Assignee: Instytut Biologii Doświadczalnej im. Marcelego Nenckiego Polska Akademia Nauk, Warsaw (PL)

( * ) Notice: Subject to any disclaimer, the term of this patent is extended or adjusted under 35 U.S.C. 154(b) by 827 days.

(21) Appl. No.: 17/298,285

(22) PCT Filed: Nov. 27, 2019

(86) PCT No.: PCT/IL2019/051298
§ 371 (c)(1),
(2) Date: May 28, 2021

(87) PCT Pub. No.: WO2020/110117
PCT Pub. Date: Jun. 4, 2020

(65) Prior Publication Data
US 2023/0054634 A1     Feb. 23, 2023

Related U.S. Application Data

(60) Provisional application No. 62/772,111, filed on Nov. 28, 2018.

(51) Int. Cl.
*A61K 38/10* (2006.01)
*A61P 35/00* (2006.01)

(52) U.S. Cl.
CPC .............. *A61K 38/10* (2013.01); *A61P 35/00* (2018.01)

(58) Field of Classification Search
CPC ......... A61K 38/10; A61K 38/00; A61P 35/00; C07K 14/535; C07K 7/08
See application file for complete search history.

(56) References Cited

PUBLICATIONS

GM-CSF Receptor Doc, 1993 (Year: 1993).*
Rafat et al., Circulating endothelial progenitor cells in malignant gliomas, J. Neurosurg, 112:43-49 (2010).
Gabrusiewicz et al., Macrophage Ablation Reduces M2-Like Populations and Jeopardizes Tumor Growth in a Mafia-Based Glioma Model1,2, Neoplasia, 17(4)374-384 (2015).
Gabrusiewicz et al., Characteristics of the Alternative Phenotype of Microglia/Macrophages and its Modulation in Experimental Gliomas, PLOS ONE, 6(8 e23902):1-12 (2011).
Sielska et al., Distinct roles of CSF family cytokines in macrophage infiltration and activation in glioma progression and injury response, Journal of Pathology, 230:310-321 (2013).
Sliwa et al., The invasion promoting effect of microglia on glioblastoma cells is inhibited by cyclosporin A, Brain, 130:476-489 (2007).
Wesolowska et al, Microglia-derived TGF-beta as an important regulator of glioblastoma invasion—an inhibition of TGF-beta-dependent effects by shRNA against human TGF-beta type II receptor, Oncogene, 27:918-930 (2008).
Markovic et al., Gliomas induce and exploit microglial MT1-MMP expression for tumor expansion, PNAS, 106(30):12530-12535 (2009).
Abramson, J. et al. Accurate structure prediction of biomolecular interactions with AlphaFold 3, Nature, vol. 630 (2024). https://doi.org/10.1038/s41586-024-07487-w.
Broughton, S.E., et al., Conformational Changes in the GM-CSF Receptor Suggest a Molecular Mechanism for Affinity Conversion and Receptor Signaling, Structure, 24(8):1271-1281 (2016). https://doi.org/10.1016/j.str.2016.05.017.
Jumper, J., et al., Highly accurate protein structure prediction with AlphaFold, Nature 596, 583-589 (2021). https://doi.org/10.1038/s41586-021-03819-2.

* cited by examiner

*Primary Examiner* — Sudhakar Katakam
(74) *Attorney, Agent, or Firm* — FISHERBROYLES, LLP; Ronni S. Jillions; Roger L. Browdy

(57) ABSTRACT

The present invention is directed to isolated peptides, compositions comprising same and methods of use thereof for treating tumors infiltrated with macrophages, such as glioblastomas.

21 Claims, 19 Drawing Sheets
Specification includes a Sequence Listing.

| Sequence | | Seq id no. |
|---|---|---|
| G7 | YQKLSYLDFQYQLD | 1 |
| A1 | AQKLSYLDFQYQLD | 7 |
| A2 | YAKLSYLDFQYQLD | 8 |
| A3 | YQALSYLDFQYQLD | 9 |
| A4 | YQKASYLDFQYQLD | 10 |
| A5 | YQKLAYLDFQYQLD | 11 |
| A6 | YQKLSALDFQYQLD | 12 |
| A7 | YQKLSYADFQYQLD | 13 |
| A8 | YQKLSYLAFQYQLD | 14 |
| A9 | YQKLSYLDAQYQLD | 15 |
| A10 | YQKLSYLDFAYQLD | 16 |
| A11 | YQKLSYLDFQAQLD | 17 |
| A12 | YQKLSYLDFQYALD | 18 |
| A13 | YQKLSYLDFQYQAD | 19 |
| A14 | YQKLSYLDFQYQLA | 20 |
| W1 | YQKLSYLDFQYQLDVHRKN | 21 |
| W2 | KQPRTYQKLSYLDFQYQLD | 22 |

Fig. 8B

SEQUENCE LISTING

<160> NUMBER OF SEQ ID NOS: 38

<210> SEQ ID NO 1
<211> LENGTH: 14
<212> TYPE: PRT
<213> ORGANISM: Artificial sequence
<220> FEATURE:
<223> OTHER INFORMATION: Synthetic -continued

<400> SEQUENCE: 1

Tyr Gln Lys Leu Ser Tyr Leu Asp Phe Gln Tyr Gln Leu Asp
1               5                   10

<210> SEQ ID NO 2
<211> LENGTH: 14
<212> TYPE: PRT
<213> ORGANISM: Artificial sequence
<220> FEATURE:
<223> OTHER INFORMATION: Synthetic

<400> SEQUENCE: 2

Gly Ser Gly Glu Gln Lys Leu Ile Ser Glu Glu Asp Leu Asn
1               5                   10

<210> SEQ ID NO 3
<211> LENGTH: 15
<212> TYPE: PRT
<213> ORGANISM: Artificial sequence
<220> FEATURE:
<223> OTHER INFORMATION: Synthetic

<400> SEQUENCE: 3

Gly Ser Gly Ser Gly Ser Gly Ser Gly His His His His His His
1               5                   10                  15

<210> SEQ ID NO 4
<211> LENGTH: 7
<212> TYPE: PRT
<213> ORGANISM: Artificial sequence
<220> FEATURE:
<223> OTHER INFORMATION: Synthetic

<400> SEQUENCE: 4

Tyr Gln Lys Leu Ser Tyr Leu
1               5

<210> SEQ ID NO 5
<211> LENGTH: 7
<212> TYPE: PRT
<213> ORGANISM: Artificial sequence
<220> FEATURE:
<223> OTHER INFORMATION: Synthetic

<400> SEQUENCE: 5

Asp Phe Gln Tyr Gln Leu Asp
1               5

<210> SEQ ID NO 6
<211> LENGTH: 7
<212> TYPE: PRT
<213> ORGANISM: Artificial sequence
<220> FEATURE:
<223> OTHER INFORMATION: Synthetic

<400> SEQUENCE: 6

Leu Ser Tyr Leu Asp Phe Gln
1               5

<210> SEQ ID NO 7
<211> LENGTH: 14
<212> TYPE: PRT
<213> ORGANISM: Artificial sequence
<220> FEATURE:
<223> OTHER INFORMATION: Synthetic -continued

```
<400> SEQUENCE: 7

Ala Gln Lys Leu Ser Tyr Leu Asp Phe Gln Tyr Gln Leu Asp
1               5                   10

<210> SEQ ID NO 8
<211> LENGTH: 14
<212> TYPE: PRT
<213> ORGANISM: Artificial sequence
<220> FEATURE:
<223> OTHER INFORMATION: Synthetic

<400> SEQUENCE: 8

Tyr Ala Lys Leu Ser Tyr Leu Asp Phe Gln Tyr Gln Leu Asp
1               5                   10

<210> SEQ ID NO 9
<211> LENGTH: 14
<212> TYPE: PRT
<213> ORGANISM: Artificial sequence
<220> FEATURE:
<223> OTHER INFORMATION: Synthetic

<400> SEQUENCE: 9

Tyr Gln Ala Leu Ser Tyr Leu Asp Phe Gln Tyr Gln Leu Asp
1               5                   10

<210> SEQ ID NO 10
<211> LENGTH: 14
<212> TYPE: PRT
<213> ORGANISM: Artificial sequence
<220> FEATURE:
<223> OTHER INFORMATION: Synthetic

<400> SEQUENCE: 10

Tyr Gln Lys Ala Ser Tyr Leu Asp Phe Gln Tyr Gln Leu Asp
1               5                   10

<210> SEQ ID NO 11
<211> LENGTH: 14
<212> TYPE: PRT
<213> ORGANISM: Artificial sequence
<220> FEATURE:
<223> OTHER INFORMATION: Synthetic

<400> SEQUENCE: 11

Tyr Gln Lys Leu Ala Tyr Leu Asp Phe Gln Tyr Gln Leu Asp
1               5                   10

<210> SEQ ID NO 12
<211> LENGTH: 14
<212> TYPE: PRT
<213> ORGANISM: Artificial sequence
<220> FEATURE:
<223> OTHER INFORMATION: Synthetic

<400> SEQUENCE: 12

Tyr Gln Lys Leu Ser Ala Leu Asp Phe Gln Tyr Gln Leu Asp
1               5                   10

<210> SEQ ID NO 13
<211> LENGTH: 14
<212> TYPE: PRT
<213> ORGANISM: Artificial sequence
<220> FEATURE:
<223> OTHER INFORMATION: Synthetic
```

-continued

```
<400> SEQUENCE: 13

Tyr Gln Lys Leu Ser Tyr Ala Asp Phe Gln Tyr Gln Leu Asp
1               5                   10

<210> SEQ ID NO 14
<211> LENGTH: 14
<212> TYPE: PRT
<213> ORGANISM: Artificial sequence
<220> FEATURE:
<223> OTHER INFORMATION: Synthetic

<400> SEQUENCE: 14

Tyr Gln Lys Leu Ser Tyr Leu Ala Phe Gln Tyr Gln Leu Asp
1               5                   10

<210> SEQ ID NO 15
<211> LENGTH: 14
<212> TYPE: PRT
<213> ORGANISM: Artificial sequence
<220> FEATURE:
<223> OTHER INFORMATION: Synthetic

<400> SEQUENCE: 15

Tyr Gln Lys Leu Ser Tyr Leu Asp Ala Gln Tyr Gln Leu Asp
1               5                   10

<210> SEQ ID NO 16
<211> LENGTH: 14
<212> TYPE: PRT
<213> ORGANISM: Artificial sequence
<220> FEATURE:
<223> OTHER INFORMATION: Synthetic

<400> SEQUENCE: 16

Tyr Gln Lys Leu Ser Tyr Leu Asp Phe Ala Tyr Gln Leu Asp
1               5                   10

<210> SEQ ID NO 17
<211> LENGTH: 14
<212> TYPE: PRT
<213> ORGANISM: Artificial sequence
<220> FEATURE:
<223> OTHER INFORMATION: Synthetic

<400> SEQUENCE: 17

Tyr Gln Lys Leu Ser Tyr Leu Asp Phe Gln Ala Gln Leu Asp
1               5                   10

<210> SEQ ID NO 18
<211> LENGTH: 14
<212> TYPE: PRT
<213> ORGANISM: Artificial sequence
<220> FEATURE:
<223> OTHER INFORMATION: Synthetic

<400> SEQUENCE: 18

Tyr Gln Lys Leu Ser Tyr Leu Asp Phe Gln Tyr Ala Leu Asp
1               5                   10

<210> SEQ ID NO 19
<211> LENGTH: 14
<212> TYPE: PRT
<213> ORGANISM: Artificial sequence
<220> FEATURE:
<223> OTHER INFORMATION: Synthetic
```

<400> SEQUENCE: 19

Tyr Gln Lys Leu Ser Tyr Leu Asp Phe Gln Tyr Gln Ala Asp
1               5                   10

<210> SEQ ID NO 20
<211> LENGTH: 14
<212> TYPE: PRT
<213> ORGANISM: Artificial sequence
<220> FEATURE:
<223> OTHER INFORMATION: Synthetic

<400> SEQUENCE: 20

Tyr Gln Lys Leu Ser Tyr Leu Asp Phe Gln Tyr Gln Leu Ala
1               5                   10

<210> SEQ ID NO 21
<211> LENGTH: 19
<212> TYPE: PRT
<213> ORGANISM: Artificial sequence
<220> FEATURE:
<223> OTHER INFORMATION: Synthetic

<400> SEQUENCE: 21

Tyr Gln Lys Leu Ser Tyr Leu Asp Phe Gln Tyr Gln Leu Asp Val His
1               5                   10                  15

Arg Lys Asn

<210> SEQ ID NO 22
<211> LENGTH: 19
<212> TYPE: PRT
<213> ORGANISM: Artificial sequence
<220> FEATURE:
<223> OTHER INFORMATION: Synthetic

<400> SEQUENCE: 22

Lys Gln Pro Arg Thr Tyr Gln Lys Leu Ser Tyr Leu Asp Phe Gln Tyr
1               5                   10                  15

Gln Leu Asp

<210> SEQ ID NO 23
<211> LENGTH: 14
<212> TYPE: PRT
<213> ORGANISM: Artificial sequence
<220> FEATURE:
<223> OTHER INFORMATION: Synthetic

<400> SEQUENCE: 23

Asn Thr Thr His Cys Leu Val Arg Trp Lys Gln Pro Arg Thr
1               5                   10

<210> SEQ ID NO 24
<211> LENGTH: 14
<212> TYPE: PRT
<213> ORGANISM: Artificial sequence
<220> FEATURE:
<223> OTHER INFORMATION: Synthetic

<400> SEQUENCE: 24

Asn His Glu Val Glu Asp Glu Ile Ile Trp Glu Glu Phe Thr
1               5                   10

<210> SEQ ID NO 25
<211> LENGTH: 14
<212> TYPE: PRT
<213> ORGANISM: Artificial sequence

```
<220> FEATURE:
<223> OTHER INFORMATION: Synthetic

<400> SEQUENCE: 25

Ile Glu Arg Phe Asn Pro Pro Ser Asn Val Thr Val Arg Cys
1               5                   10

<210> SEQ ID NO 26
<211> LENGTH: 14
<212> TYPE: PRT
<213> ORGANISM: Artificial sequence
<220> FEATURE:
<223> OTHER INFORMATION: Synthetic

<400> SEQUENCE: 26

Arg Trp Lys Gln Pro Arg Thr Tyr Gln Lys Leu Ser Tyr Leu
1               5                   10

<210> SEQ ID NO 27
<211> LENGTH: 14
<212> TYPE: PRT
<213> ORGANISM: Artificial sequence
<220> FEATURE:
<223> OTHER INFORMATION: Synthetic

<400> SEQUENCE: 27

His Ser Val Lys Ile Arg Ala Ala Asp Val Arg Ile Leu Asn
1               5                   10

<210> SEQ ID NO 28
<211> LENGTH: 14
<212> TYPE: PRT
<213> ORGANISM: Artificial sequence
<220> FEATURE:
<223> OTHER INFORMATION: Synthetic

<400> SEQUENCE: 28

Ala Asp Val Arg Ile Leu Asn Trp Ser Ser Trp Ser Glu Ala
1               5                   10

<210> SEQ ID NO 29
<211> LENGTH: 14
<212> TYPE: PRT
<213> ORGANISM: Artificial sequence
<220> FEATURE:
<223> OTHER INFORMATION: Synthetic

<400> SEQUENCE: 29

Trp Ser Ser Trp Ser Glu Ala Ile Glu Phe Gly Ser Asp Asp
1               5                   10

<210> SEQ ID NO 30
<211> LENGTH: 14
<212> TYPE: PRT
<213> ORGANISM: Artificial sequence
<220> FEATURE:
<223> OTHER INFORMATION: Synthetic

<400> SEQUENCE: 30

Val Leu Gly Phe Leu Phe Lys Arg Phe Leu Arg Ile Gln Arg
1               5                   10

<210> SEQ ID NO 31
<211> LENGTH: 14
<212> TYPE: PRT
<213> ORGANISM: Artificial sequence
<220> FEATURE:
```

```
<223> OTHER INFORMATION: Synthetic

<400> SEQUENCE: 31

Arg Phe Leu Arg Ile Gln Arg Leu Phe Pro Pro Val Pro Gln
1               5                   10

<210> SEQ ID NO 32
<211> LENGTH: 15
<212> TYPE: PRT
<213> ORGANISM: Artificial sequence
<220> FEATURE:
<223> OTHER INFORMATION: Synthetic

<400> SEQUENCE: 32

Lys Tyr Gln Lys Leu Ser Tyr Leu Asp Phe Gln Tyr Gln Leu Asp
1               5                   10                  15

<210> SEQ ID NO 33
<211> LENGTH: 14
<212> TYPE: PRT
<213> ORGANISM: Artificial sequence
<220> FEATURE:
<223> OTHER INFORMATION: Synthetic

<400> SEQUENCE: 33

Tyr Lys Lys Leu Ser Tyr Leu Asp Phe Gln Tyr Gln Leu Asp
1               5                   10

<210> SEQ ID NO 34
<211> LENGTH: 14
<212> TYPE: PRT
<213> ORGANISM: Artificial sequence
<220> FEATURE:
<223> OTHER INFORMATION: Synthetic

<400> SEQUENCE: 34

Tyr Gln Lys Leu Ser Tyr Leu Asp Phe Gln Lys Gln Leu Asp
1               5                   10

<210> SEQ ID NO 35
<211> LENGTH: 14
<212> TYPE: PRT
<213> ORGANISM: Artificial sequence
<220> FEATURE:
<223> OTHER INFORMATION: Synthetic

<400> SEQUENCE: 35

Tyr Gln Lys Leu Ser Tyr Leu Asp Phe Gln Tyr Gln Lys Asp
1               5                   10

<210> SEQ ID NO 36
<211> LENGTH: 15
<212> TYPE: PRT
<213> ORGANISM: Artificial sequence
<220> FEATURE:
<223> OTHER INFORMATION: Synthetic

<400> SEQUENCE: 36

Tyr Gln Lys Leu Ser Tyr Leu Asp Phe Gln Tyr Gln Lys Asp Lys
1               5                   10                  15

<210> SEQ ID NO 37
<211> LENGTH: 15
<212> TYPE: PRT
<213> ORGANISM: Artificial sequence
<220> FEATURE:
<223> OTHER INFORMATION: Synthetic
```

-continued

```
<400> SEQUENCE: 37

Lys Tyr Gln Lys Leu Ser Tyr Ala Asp Phe Gln Tyr Gln Leu Asp
1               5                   10                  15

<210> SEQ ID NO 38
<211> LENGTH: 15
<212> TYPE: PRT
<213> ORGANISM: Artificial sequence
<220> FEATURE:
<223> OTHER INFORMATION: Synthetic

<400> SEQUENCE: 38

Lys Tyr Gln Lys Ala Ser Tyr Ala Asp Phe Gln Tyr Gln Leu Asp
1               5                   10                  15
```

COMPOSITIONS AND METHODS FOR TREATING GLIOMA

The Sequence Listing in ASCII text file format of 8,748 bytes in size, created on Dec. 8, 2021, with the file name "2021-12-20SequenceListing_KAMINSKA1," filed in the U.S. Patent and Trademark Office on even date herewith, is hereby incorporated herein by reference.

FIELD OF THE INVENTION

The present invention is directed to isolated peptides, compositions comprising same and methods of use thereof for treating tumors infiltrated with macrophages, such as glioblastomas.

BACKGROUND OF THE INVENTION

Malignant gliomas account for about 80% of primary brain tumors in adults. The most frequent and malignant is glioblastoma (GBM, WHO grade IV), a very aggressive, highly diffusive brain tumor, which due to a late diagnosis and the lack of efficient therapy remains incurable. The current management of glioblastoma consists of surgery, radiotherapy and chemotherapy, but due to ineffective tumor removal and therapy resistance, tumors invariably recur in 6 months and a median survival of GBM patients is 14 months.

It has been found that glioma cells attract brain resident (microglia) and peripheral macrophages to a tumor, turn them into pro-invasive cells that are indispensable for tumor invasion and progression (Sliwa et al., Brain, 130: 476-489, 2007; Wesolowska et al., Oncogene, 27: 918-930, 2008; Markovic et al., PNAS, 106(30): 12530-12535, 2009; Gabrusiewicz et al., PlosONE, 6(8): e23902, 2011; Gabrusiewicz et al., Neoplasia, 17(4): 374-384, 2015). Moreover, glioma cells overexpress and secrete proteins and cytokines that reprogram brain macrophages into cells that support invasion, angiogenesis and suppress anti-tumor immunity. One of the factors triggering those responses was identified as glioma-derived granulocyte macrophage colony-stimulating factor—GM-CSF (Csf-2). Stable knockdown of Csf-2 in rodent GL261 glioma cells reduced intracranial glioma growth and inhibited pro-tumorigenic accumulation and polarization of microglia/macrophages in animal gliomas (Sielska et al., J. Pathol., 230: 310-321, 2013).

U.S. Pat. No. 9,453,050 discloses peptides capable of blocking Spp1 (also known as osteopontin, OPN or secreted protein 1) and Csf-2 (also known as granulocyte macrophage colony-stimulating factor or GM-CSF) and use thereof for treating GBM.

There is an unmet need for effective GBM therapies.

SUMMARY OF THE INVENTION

Provided herein are isolated peptides, compositions comprising same and methods of using thereof for treating a subject having GBM. The peptides disclosed herein interfere with GM-CSF, and its receptor interaction and thus block the signaling pathways crucial for glioma invasiveness and progression. Surprisingly, the peptides selectively bind to GM-CSF protein, block its binding to respective receptors on microglia, and inhibit activation of the receptors and downstream signaling pathways resulting in inhibition of glioma invasiveness and growth. Thus, the peptides disclosed herein provide a new highly specific glioblastoma therapy.

Moreover, the peptides disclosed herein, in particular the peptides comprising SEQ ID NOs: 1, 23 and 24, exhibited strong and selective binding to GM-CSF, and reduced microglia-dependent invasion in vitro. A representative peptide, G7 (SEQ ID NO: 1), was also shown to block microglia-dependent invasion in glioma cell lines and patient-derived cell cultures. Unexpectedly, this peptide was also shown to exhibit anti-tumor activity in vivo.

In some embodiments, there is provided an isolated artificial peptide for inhibiting GM-CSF activity, said peptide comprises an amino acid sequence set forth in SEQ ID NO: 1 or a variant thereof, an amino acid sequence set forth in SEQ ID NO: 23, and an amino acid sequence set forth in SEQ ID NO: 24; wherein said peptide is of 10-20 amino acids, and wherein the variant of SEQ ID NO: 1 is selected from SEQ ID NO: 1 with substitution of amino acids in any one or more of positions 2, 3, 5, 6, 9 and 11-13 with alanine or lysine and/or addition of lysine at the N-terminus of SEQ ID NO: 1. Each possibility represents a separate embodiment of the present invention.

In some embodiments, there is provided an isolated artificial peptide for inhibiting GM-CSF activity, said peptide comprising an amino acid sequence selected from the group consisting of: an amino acid sequence set forth in SEQ ID NO: 1 and variants thereof, an amino acid sequence set forth in SEQ ID NO: 23, and an amino acid sequence set forth in SEQ ID NO: 24; wherein said peptide is of 10-20 amino acids, and wherein each of the variants of SEQ ID NO: 1 is selected from SEQ ID NO: 1 with substitution of amino acids in any one or more of positions 2, 3, 5, 6, 9 and 11-13 with alanine or lysine and/or addition of lysine at the N-terminus of SEQ ID NO: 1. Each possibility represents a separate embodiment of the present invention.

In some embodiments, the isolated artificial peptide comprises SEQ ID NO: 1 or variants thereof.

In some embodiments, the isolated artificial peptide is consisting of SEQ ID NO: 1 or variants thereof.

In some embodiments, the isolated artificial peptide comprises SEQ ID NO: 1, SEQ ID NO: 8, SEQ ID NO: 9, SEQ ID NO: 11, SEQ ID NO: 12, SEQ ID NO: 15, SEQ ID NO: 17, SEQ ID NO:18, SEQ ID NO: 19, SEQ ID NO: 32 or SEQ ID NO: 35. Each possibility represents a separate embodiment.

In some embodiments, the isolated artificial peptide is consisting of SEQ ID NO: 1, SEQ ID NO: 8, SEQ ID NO: 9, SEQ ID NO: 11, SEQ ID NO: 12, SEQ ID NO: 15, SEQ ID NO: 17, SEQ ID NO:18, SEQ ID NO: 19, SEQ ID NO: 32 or SEQ ID NO: 35. Each possibility represents a separate embodiment.

In some embodiments, said isolated artificial peptide comprising a variant of SEQ ID NO: 1 selected from SEQ ID NO: 8, SEQ ID NO: 9, SEQ ID NO: 11, SEQ ID NO: 12, SEQ ID NO: 15, SEQ ID NO: 17, SEQ ID NO:18, SEQ ID NO: 19, SEQ ID NO: 32 and SEQ ID NO: 35. Each possibility represents a separate embodiment.

In some embodiments, said isolated artificial peptide is consisting of a variant of SEQ ID NO: 1 selected from SEQ ID NO: 8, SEQ ID NO: 9, SEQ ID NO: 11, SEQ ID NO: 12, SEQ ID NO: 15, SEQ ID NO: 17, SEQ ID NO:18, SEQ ID NO: 19, SEQ ID NO: 32 and SEQ ID NO: 35. Each possibility represents a separate embodiment.

In some embodiments, the isolated artificial peptide comprises SEQ ID NO: 1, SEQ ID NO: 8, SEQ ID NO: 17, SEQ ID NO:18, SEQ ID NO: 19, SEQ ID NO: 32 or SEQ ID NO: 35. Each possibility represents a separate embodiment.

In some embodiments, the isolated artificial peptide is consisting of SEQ ID NO: 1, SEQ ID NO: 8, SEQ ID NO: 17, SEQ ID NO:18, 19, SEQ ID NO: 32 or SEQ ID NO: 35. Each possibility represents a separate embodiment.

In some embodiments, the isolated artificial peptide comprises SEQ ID NO: 1. In some embodiments, the isolated artificial peptide comprises SEQ ID NO: 8. In some embodiments, the isolated artificial peptide comprises SEQ ID NO: 9. In some embodiments, the isolated artificial peptide comprises SEQ ID NO: 11. In some embodiments, the isolated artificial peptide comprises SEQ ID NO: 12. In some embodiments, the isolated artificial peptide comprises SEQ ID NO: 15. In some embodiments, the isolated artificial peptide comprises SEQ ID NO: 17. In some embodiments, the isolated artificial peptide comprises SEQ ID NO:18. In some embodiments, the isolated artificial peptide comprises SEQ ID NO: 19. In some embodiments, the isolated artificial peptide comprises SEQ ID NO: 32. In some embodiments, the isolated artificial peptide comprises SEQ ID NO: 35.

In some embodiments, the isolated artificial peptide is consisting of SEQ ID NO: 1. In some embodiments, the isolated artificial peptide is consisting of SEQ ID NO: 8. In some embodiments, the isolated artificial peptide comprises SEQ ID NO: 9. In some embodiments, the isolated artificial peptide is consisting of SEQ ID NO: 11. In some embodiments, the isolated artificial peptide is consisting of SEQ ID NO: 12. In some embodiments, the isolated artificial peptide is consisting of SEQ ID NO: 15. In some embodiments, the isolated artificial peptide is consisting of SEQ ID NO: 17. In some embodiments, the isolated artificial peptide is consisting of SEQ ID NO:18. In some embodiments, the isolated artificial peptide is consisting of SEQ ID NO: 19. In some embodiments, the isolated artificial peptide comprises SEQ ID NO: 32. In some embodiments, the isolated artificial peptide is consisting of SEQ ID NO: 35.

In some embodiments, the isolated artificial peptide is consisting of an amino acid sequence set forth in SEQ ID NO: 23, or an amino acid sequence set forth in SEQ ID NO: 24. Each possibility represents a separate embodiment of the present invention.

In some embodiments, the isolated artificial peptide comprises the sequence set forth in SEQ ID NO: 23, or an analog or derivative thereof.

In some embodiments, the isolated artificial peptide comprises the sequence set forth in SEQ ID NO: 24, or an analog or derivative thereof.

In some embodiments, the artificial peptide is essentially consisting of the sequence set forth in SEQ ID NO: 1, or an analog or derivative thereof.

In some embodiments, the artificial peptide is essentially consisting of the sequence set forth in SEQ ID NO: 23, or an analog or derivative thereof.

In some embodiments, the artificial peptide is essentially consisting of the sequence set forth in SEQ ID NO: 24, or an analog or derivative thereof.

In some embodiments, the isolated artificial peptide is consisting of the sequence set forth in SEQ ID NO: 1, or an analog or derivative thereof.

In some embodiments, the isolated artificial peptide is consisting of the sequence set forth in SEQ ID NO: 23, or an analog or derivative thereof.

In some embodiments, the isolated artificial peptide is consisting of the sequence set forth in SEQ ID NO: 24, or an analog or derivative thereof.

In some embodiments, the isolated artificial peptide is fused to a peptide assisting transport through the blood brain barrier (BBB).

In some embodiments, the isolated artificial peptide is a cyclic peptide.

In some embodiments, there is provided a pharmaceutical composition comprising at least one of the isolated artificial peptides disclosed herein and a pharmaceutical acceptable carrier.

In some embodiments, there is provided a pharmaceutical composition comprising at least one of the isolated peptides disclosed herein and a pharmaceutical acceptable carrier for inhibiting binding of GM-CSF to its receptor.

In some embodiments, there is provided a pharmaceutical composition comprising at least one of the isolated peptides disclosed herein and a pharmaceutical acceptable carrier for inhibiting cellular migration.

According to some embodiments, inhibiting cellular migration comprises inhibiting migration of tumor cells from the tumor to other tissues. According to some embodiments, the tumor is glioma.

In some embodiments, there is provided a pharmaceutical composition comprising at least one of the isolated peptides disclosed herein and a pharmaceutical acceptable carrier for treating glioma. In some embodiments, there is provided a pharmaceutical composition comprising at least one of the isolated peptides disclosed herein and a pharmaceutical acceptable carrier for the treatment of glioma. In some embodiments, there is provided a pharmaceutical composition comprising at least one of the isolated peptides disclosed herein and a pharmaceutical acceptable carrier for use in the treatment of glioma. In some embodiments, there is provided a pharmaceutical composition at least one of the isolated peptides disclosed herein and a pharmaceutical acceptable carrier for the preparation of a medicament for the treatment of glioma.

In some embodiments, said glioma is selected from the group consisting of: ependymoma, astrocytoma, oligodendroglioma, glioblastoma, or a mixed glioma. Each possibility represents a separate embodiment of the present invention.

In some embodiments, said glioma is ependymoma. In some embodiments, said glioma is astrocytoma. In some embodiments, said glioma is oligodendroglioma. In some embodiments, said glioma is glioblastoma. In some embodiments, said glioma is a mixed glioma.

In some embodiments, there is provided a method of treating glioma comprising administering to a subject in need thereof a therapeutically effective amount of a pharmaceutical composition comprising a peptide capable of inhibiting GM-CSF activity, wherein said peptide comprises a sequence selected from the group consisting of: an amino acid sequence set forth in SEQ ID NO: 1, an amino acid sequence set forth in SEQ ID NO: 23, and an amino acid sequence set forth in SEQ ID NO: 24, wherein the variants of SEQ ID NO: 1 are selected from SEQ ID NO: 1 with substitution of amino acids in any one or more of positions 2, 3, 5, 6, 9 and 11-13 with alanine or lysine and/or addition of lysine at the N-terminus of SEQ ID NO: 1. Each possibility represents a separate embodiment of the present invention.

In some embodiments, said treating glioma is selected from the group consisting of:

reducing phagocytosis, reducing motility, reducing proliferation of tumor infiltrating macrophages having pro-tumor activity, and reducing secretion of pro-inflammatory cytokines or chemokines by macrophages. Each possibility represents a separate embodiment of the present invention.

According to some embodiments, treating glioma comprises inhibiting migration of tumor cells from the tumor to the cerebrospinal fluid.

In some embodiments, there is provided a kit for the treatment of glioma comprising a pharmaceutical composition comprising a peptide capable of inhibiting GM-CSF activity, wherein said peptide comprises a sequence selected from the group consisting of: an amino acid sequence set forth in SEQ ID NO: 1, an amino acid sequence set forth in SEQ ID NO: 23, and an amino acid sequence set forth in SEQ ID NO: 24, and instructions for use of said kit, wherein the variants of SEQ ID NO: 1 are selected from SEQ ID NO: 1 with substitution of amino acids in any one or more of positions 2, 3, 5, 6, 9 and 11-13 with alanine or lysine and/or addition of lysine at the N-terminus of SEQ ID NO: 1. Each possibility represents a separate embodiment of the present invention.

Other objects, features and advantages of the present invention will become clear from the following description.

U87 MG cells invading without microglia cells representing basal invasion of glioma cells; Ctrl⁺: U87 MG cells invading in the presence of microglia cells, set as 100%; DMSO (black bars): Ctrl conditioned with a corresponding solvent dose. Data are presented as means +/−s.d. (error bars) and were calculated with three independent biological experiments.

Figure 5A:
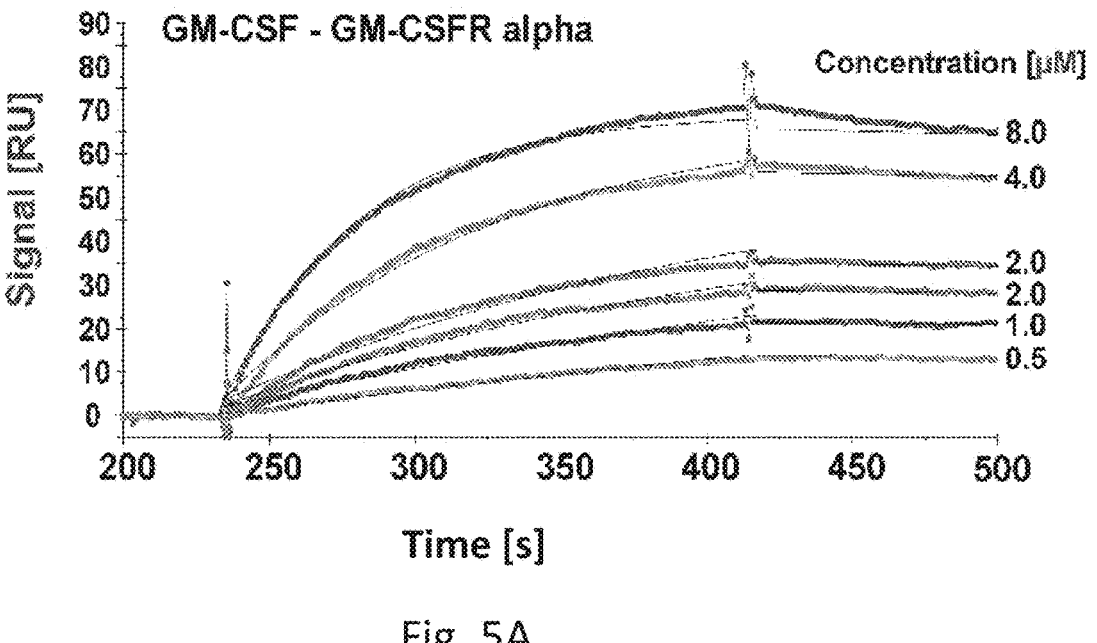

FIG. 5A presents binding of GM-CSFR alpha with increasing concentrations of GM-CSF.

Figure 5B:
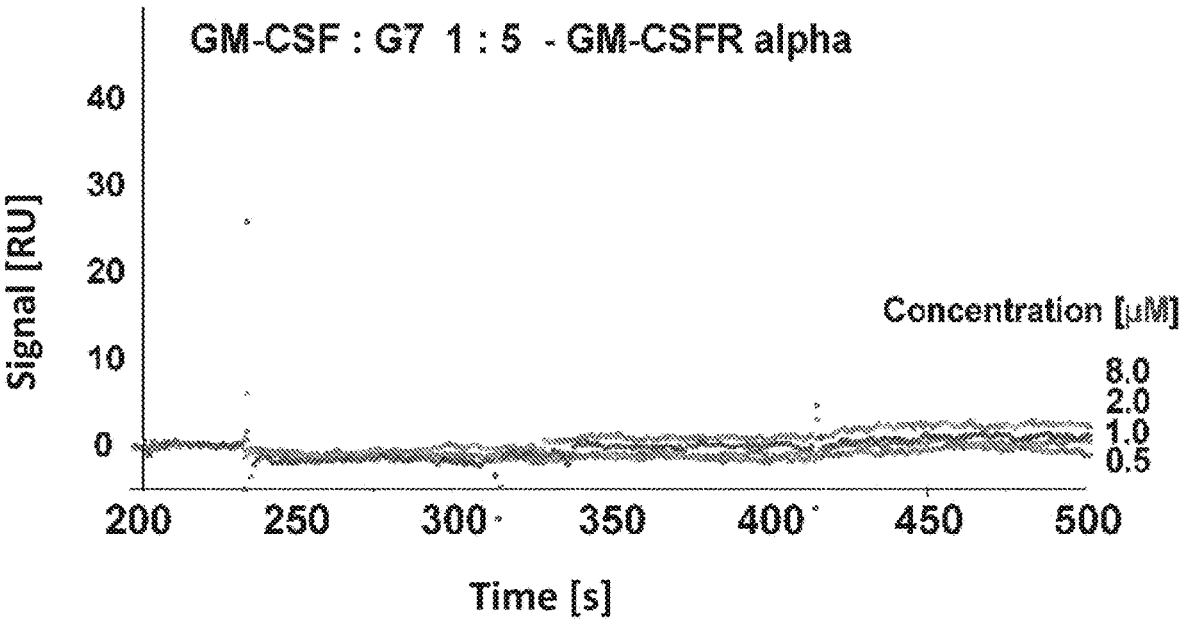

FIG. 5B presents binding of GM-CSF to its receptor, GM-CSFR alpha subunit, co-administered with G7 peptide (SEQ ID NO: 1) at a ratio 1:5.

Figure 6A:
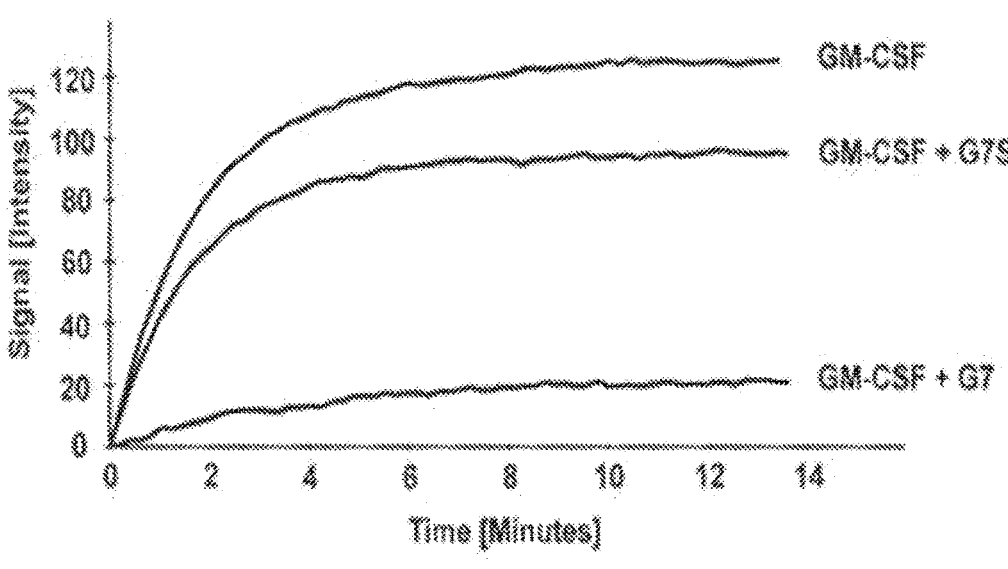

FIG. 6A presents real-time binding of GM-CSF to U937 cells in the presence of G7 (SEQ ID NO: 1) or G7S or under control conditions (without peptides).

Figure 6B:
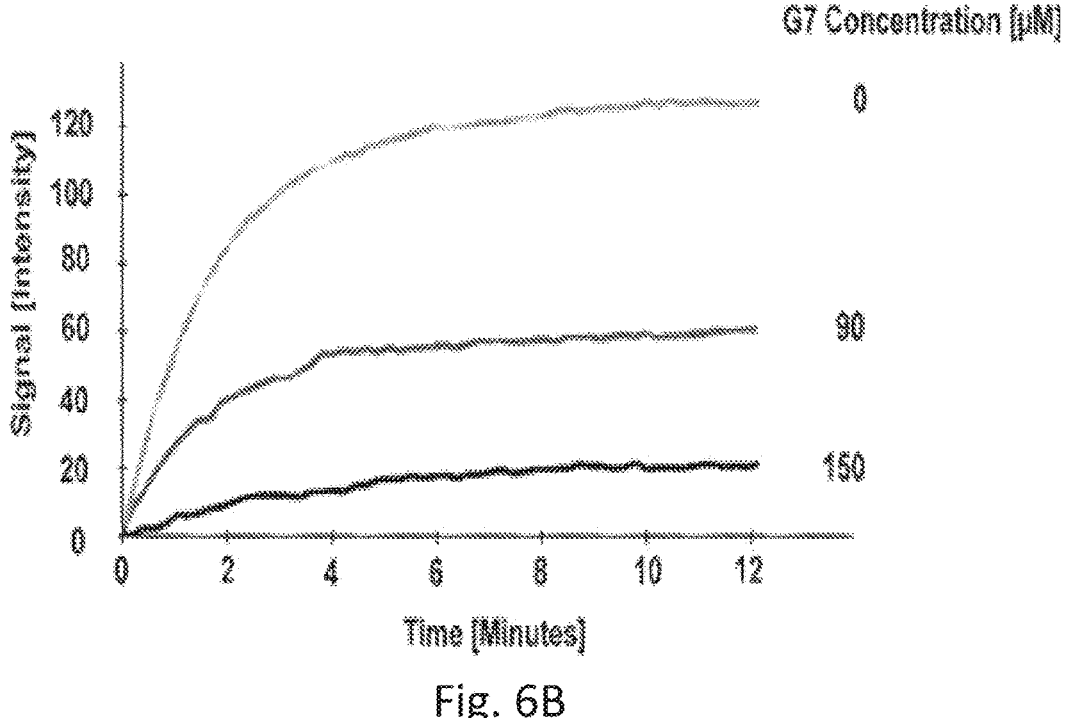

FIG. 6B presents concentration dependent G7-driven inhibition of GM-CSF binding to its receptor on U937 cells.

Figures 7, 8A:
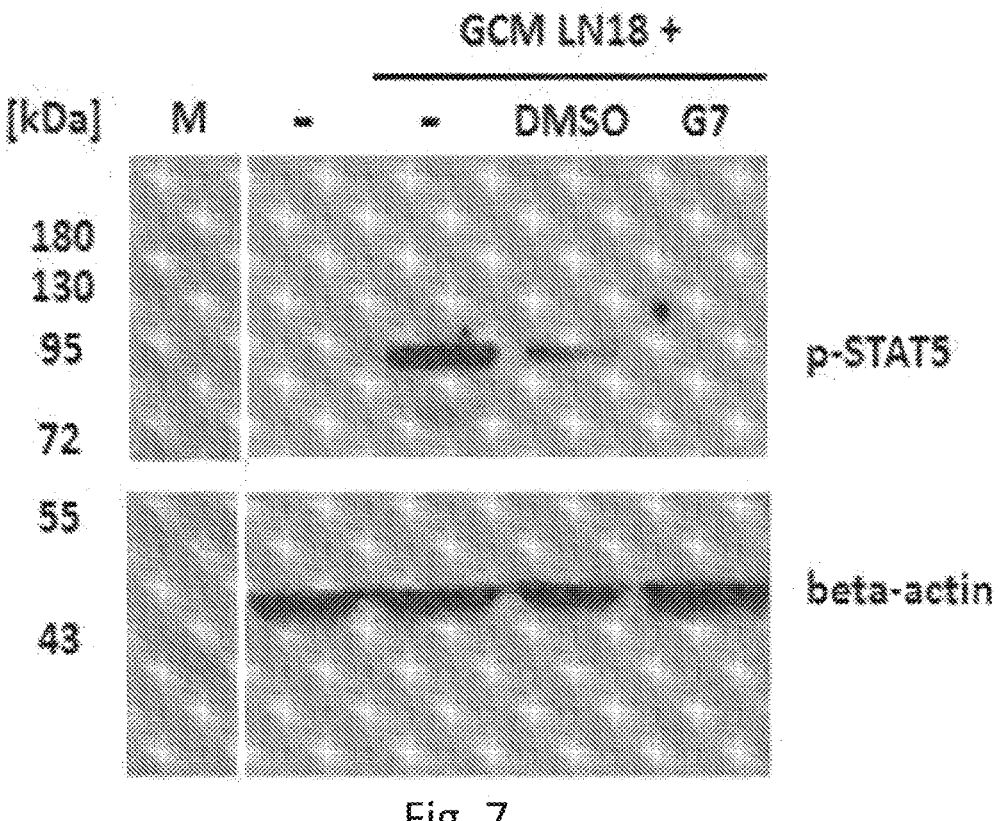

FIG. 7 presents Western blot analysis of STAT5 phosphorylation induced by Glioma conditioned medium in the presence or absence of G7 peptide (SEQ ID NO: 1) using beta-actin detection to ensure equal quantities of loaded total protein extracts.

FIG. 8A presents GM-CSF binding by G7 short variants (SEQ ID NOs: 4-6) analyzed using ELISA.

FIG. 8B presents peptide sequences of G7 peptide (SEQ ID NO: 1) and alanine variants thereof (SEQ ID Nos: 7-22).

Figure 8C:
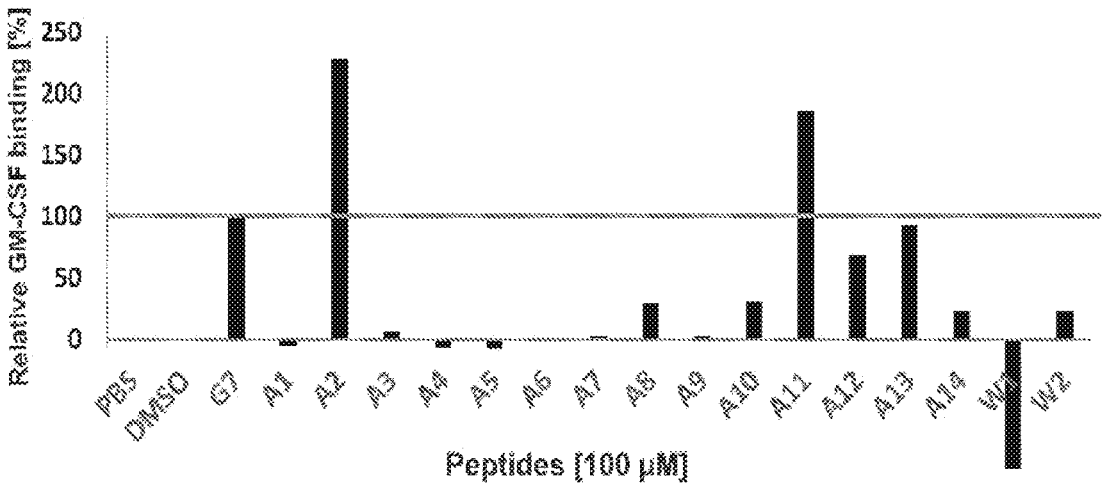

FIG. 8C presents GM-CSF binding by G7 variants shown in FIG. 8B, analyzed using ELISA.

Figure 8D:
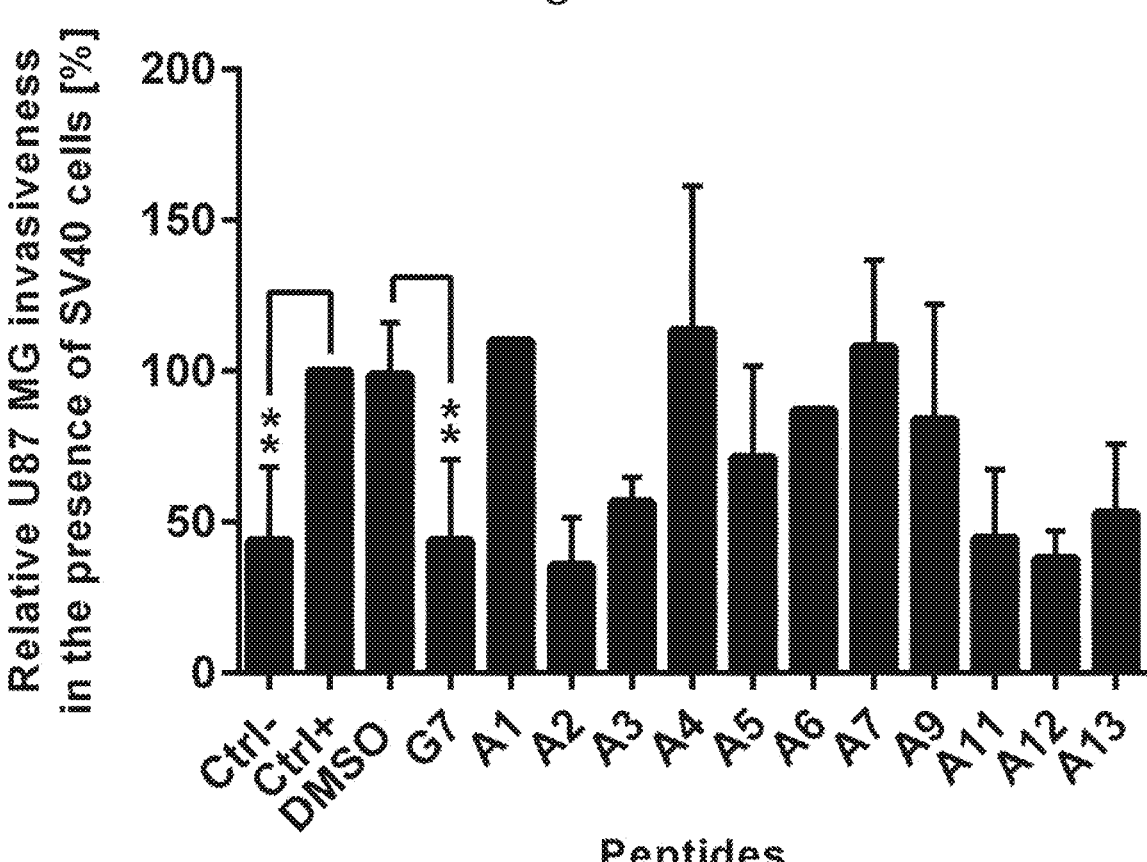

FIG. 8D presents the effect of certain G7 alanine variants on the invasion of U87 MG cells induced by the presence of SV40 microglial cells (**=p<0.01).

Figures 9, 10:
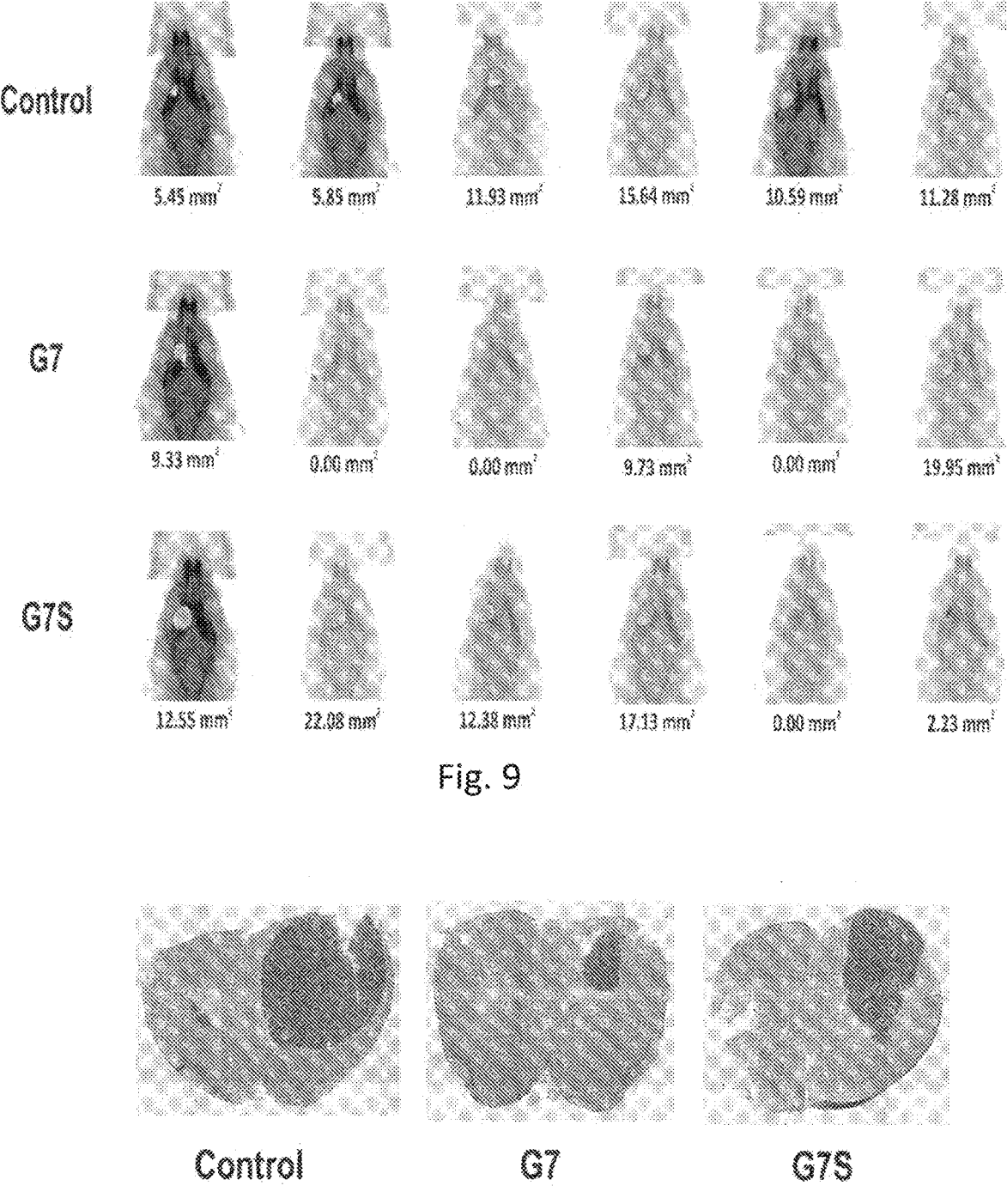

FIG. 9 presents volume of U87-MG-RFP gliomas transplanted in nude mice, measured in vivo using fluorescence imaging with Xtreme Brucker system, devoid of treatment and in the presence of G7 or G7S peptides.

FIG. 10 presents representative images of histological sections of the tumor-bearing mice brains (untreated (control), and G7 and G7S-treated mice). Sections were stained with toluidine blue, images were scanned using automated Leica DM4000 B (10× magnification).

Figure 11:
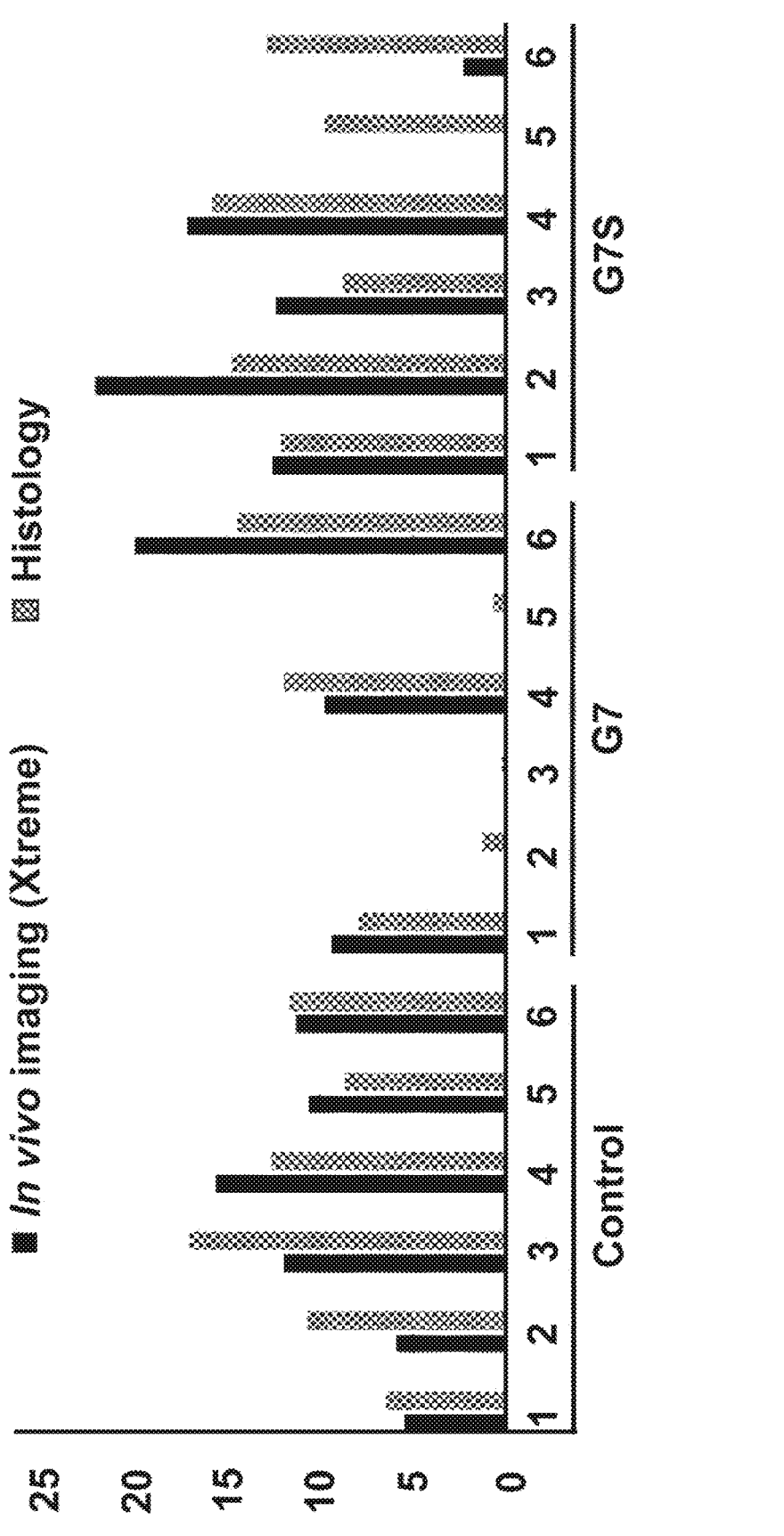

FIG. 11 presents relative tumor (control, G7 and G7S) volume measurements obtained by In-Vivo Xtreme fluorescence imaging (black bars) and calculated from histological staining of tumor sections using Leica DM4000 B microscope software (textured bars).

Figure 12:
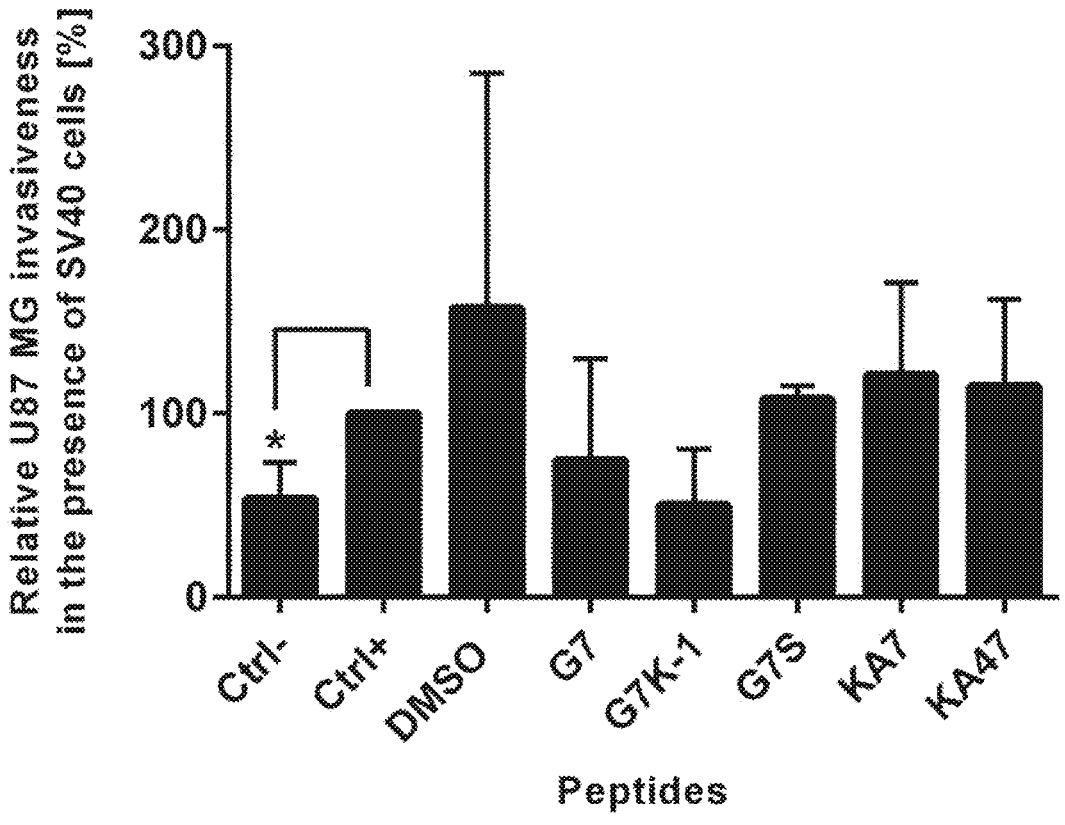

FIG. 12 presents the effect of G7 variants (G7K-1—SEQ ID NO: 32; G7S—control peptides (scrambled peptides); KA7—SEQ ID NO: 37 and KA47—SEQ ID NO: 38) on the invasion of U87 MG cells induced by the presence of SV40 microglial cells (*=p<0.05).

DETAILED DESCRIPTION

Disclosed herein is a therapeutic strategy using short interfering peptides that block the signaling pathway crucial for glioma invasiveness and progression. Thus, provided herein are peptides, compositions comprising same and methods of using thereof for treating a subject having a tumor that is infiltrated with macrophages ("infiltrating macrophages"), e.g. microglia having pro-tumoral activity. Infiltrating macrophages having pro-tumoral activity may participate in matrix remodeling, invasion, angiogenesis and suppression of adaptive immunity and may proliferate, be phagocytic and be mobile. Infiltrating macrophages with pro-tumoral activity, and may contribute to the growth or maintenance of the tumor, are present in tumors, such as malignant tumors, e.g., brain tumors, such as gliomas. It has been shown that the innate immune cells: brain resident and peripheral macrophages, accumulate in malignant gliomas and are indispensable for tumor invasion and growth.

In some embodiments, there is provided an isolated peptide for inhibiting GM-CSF activity.

It is to be understood that any one of the isolated peptides disclosed herein is artificial. Each of the peptides disclosed herein is artificially synthesized wherein any method known in the art for peptide synthesis applies.

Granulocyte Macrophage Colony Stimulating Factor is also referred to as "GM-CSF" as well as CSF2, molgramostin and sargramostin, and has Gene ID: 1437 and MIM: 138960. The active form of the protein is found extracellularly as a homodimer. The amino-acid sequence of the human GM-CSF precursor protein is provided under GenBank Accession No. NP_000749.2 (SEQ ID NO: 16), and is encoded by the nucleotide sequence provided under GenBank Accession No. NM_000758.2.

GM-CSF binds its receptor, also referred to as CSF2RA, CD116, CDw116, CSF2R, CSF2RAX, CSF2RAY, CSF2RX, CSF2RY, GM-CSF-R-alpha, GMCSFR, GMRa and SMDP4, having Gene ID: 1430. The amino acid sequences of the precursor of the human isoforms are provided under GenBank Accession Nos: NP_001155001.1, NP_001155002.1, NP_001155003.1, NP_001155004.1, NP_006131.2, NP_758448.1, NP_758449.1, NP_758450.1, and NP_758452.1.

As used herein, the terms "peptide for inhibiting GM-CSF activity" and "GM-CSF inhibitor" are interchangeable and refer to an agent, such as a peptide, that is capable of inhibiting, or reducing significantly, at least one biological activity of GM-CSF. According to some embodiments, a GM-CSF inhibitor is an agent that inhibits the progression of a tumor, e.g., a glioma, such as by slowing-down tumor progression by at least 10%, 20%, 30%, 40%, 50%, 60%, 70%, 80%, 90%, 95%, 99% or 100%, relative to tumor progression in the absence of the GM-CSF inhibitor. Each possibility represents a separate embodiment of the present invention.

The GM-CSF inhibitor disclosed herein can also be an inhibitor that stabilizes tumor (e.g., glioma) size or reduces it by at least 10%, 20%, 30%, 40%, 50%, 60%, 70%, 80%, 90%, 95%, 99% 100% (2-fold), 3-fold, 5-fold or more. Each possibility represents a separate embodiment of the present invention.

The GM-CSF inhibitor disclosed herein can exhibit any one or more of anti-tumor activities, such as, reduce tumor invasion by macrophages or microglia; reduce stimulation and/or transformation of tumor infiltrating macrophages into cells having pro-tumor activity;

and/or reduce angiogenesis in the tumor. The GM-CSF inhibitor disclosed herein may have one of the following characteristics: (i) block GM-CSF production or synthesis, e.g., by tumor cells; (ii) neutralize the activity of GM-CSF; (iii) prevent (or inhibit) the binding of GM-CSF to its receptor; (iv) inhibit the signal transduction pathway that is activated by the binding of GM-CSF to its receptor on macrophages or microglia or (v) or inhibit GM-CSF receptor production or synthesis, e.g., in macrophages or microglia. In some embodiments, the GM-CSF inhibitor disclosed herein is protein or peptide based. In some embodiments, the GM-CSF inhibitor is an agent that inhibits the expression of the GM-CSF, e.g., an inhibitory nucleic acid, e.g., an siRNA, shRNA, antisense molecule, a ribozyme or an aptamer. An "agent" as used herein refers to any type of molecule or complex of molecules, such as macromolecules or small molecules.

The GM-CSF inhibitor disclosed herein may inhibit a biological activity of GM-CSF by at least 10%, 20%, 30%, 40%, 50%, 60%, 70%, 80%, 90%, 95%, 99% or 100%. Each possibility represents a separate embodiment of the present invention. For example, a GM-CSF inhibitor may reduce the interaction between GM-CSF and its receptor by a factor of at least 10%, 20%, 30%, 40%, 50%, 60%, 70%, 80%, 90%, 95%, 99% or 100%. The GM-CSF inhibitor may also be an agent that blocks the expression of the GM-CSF protein or GM-CSF receptor (e.g., a chain) and may, e.g., reduce its expression by a factor of at least 10%, 20%, 30%, 40%, 50%, 60%, 70%, 80%, 90%, 95%, 99% or 100%. Each possibility represents a separate embodiment of the present invention.

In some embodiments, said isolated artificial peptide for inhibiting GM-CSF activity comprises an amino acid sequence selected from the group consisting of: an amino acid sequence set forth in SEQ ID NO: 1 or variants thereof, an amino acid sequence set forth in SEQ ID NO: 23, and an amino acid sequence set forth in SEQ ID NO: 24, wherein each of the variants of SEQ ID NO: 1 is selected from SEQ ID NO: 1 with substitution of amino acids in any one or more of positions 2, 3, 5, 6, 9 and 11-13 with alanine or lysine and/or addition of lysine at the N-terminus of SEQ ID NO: 1. Each possibility represents a separate embodiment of the present invention.

Position number indicates the position of the amino acid where the modification takes place, wherein the first amino acid in the amino acid chain of the peptides disclosed herein is the amino acid at the N-terminus, which is considered as having position 1 (e.g. Tyrosine in SEQ ID NO. 1).

In some embodiments, the isolated artificial peptide comprises SEQ ID NO: 1 or variants thereof.

In some embodiments, the isolated artificial peptide is consisting of SEQ ID NO: 1 or variants thereof.

Thus, according to some embodiments, said isolated artificial peptide for inhibiting GM-CSF activity comprises an amino acid sequence as set forth in SEQ ID NO: 1 or variants thereof, wherein the variants are selected peptides having substitution of amino acids in any one or more of positions 2, 3, 5, 6, 9 and 11-13 with alanine or lysine and/or addition of lysine at the N-terminus corresponding to the original amino acid chain of SEQ ID NO: 1.

According to some embodiments, said isolated artificial peptide for inhibiting GM-CSF activity comprises a variant of SEQ ID NO: 1, wherein the variant is a peptide having substitution of amino acids in at least one of positions 2, 3, 5, 6, 9 and 11-13 with alanine or lysine and/or addition of lysine at the N-terminus corresponding to the original amino acid chain of SEQ ID NO: 1. Each possibility represents a separate embodiment.

According to some embodiments, said isolated artificial peptide for inhibiting GM-CSF activity comprises a variant of SEQ ID NO: 1, wherein the variant is a peptide having SEQ ID NO: 1 substituted with alanine or lysine in at least one of positions 2, 3, 5, 6, 9 and 11-13 or SEQ ID NO: 1 with the addition of lysine at the N-terminus. Each possibility represents a separate embodiment.

According to some embodiments, said isolated artificial peptide for inhibiting GM-CSF activity comprises a variant of SEQ ID NO: 1, wherein the variant is a peptide having SEQ ID NO: 1 substituted with alanine in at least one of positions 2, 3, 5, 6, 9 and 11-13. Each possibility represents a separate embodiment.

According to some embodiments, said isolated artificial peptide for inhibiting GM-CSF activity comprises a variant of SEQ ID NO: 1, wherein the variant is a peptide having SEQ ID NO: 1 substituted with alanine in one of the following positions 2, 3, 5, 6, 9 and 11-13. Each possibility represents a separate embodiment.

According to some embodiments, said isolated artificial peptide for inhibiting GM-CSF activity comprises a variant of SEQ ID NO: 1, wherein the variant is a peptide having SEQ ID NO: 1 substituted with lysine in at least one of positions 2 and 13.

According to some embodiments, said isolated artificial peptide for inhibiting GM-CSF activity comprises a variant of SEQ ID NO: 1, with one or more of the following modifications: substitution with lysine in position 2, substitution with lysine in position 13 and addition of lysine at the N-terminus.

In some embodiments, the isolated artificial peptide comprises SEQ ID NO: 1, SEQ ID NO: 8, SEQ ID NO: 9, SEQ ID NO: 11, SEQ ID NO: 12, SEQ ID NO: 15, SEQ ID NO: 17, SEQ ID NO:18, SEQ ID NO: 19, SEQ ID NO: 32 or SEQ ID NO: 35. Each possibility represents a separate embodiment.

In some embodiments, the isolated artificial peptide is consisting of SEQ ID NO: 1, SEQ ID NO: 8, SEQ ID NO: 9, SEQ ID NO: 11, SEQ ID NO: 12, SEQ ID NO: 15, SEQ ID NO: 17, SEQ ID NO:18, SEQ ID NO: 19, SEQ ID NO: 32 or SEQ ID NO: 35. Each possibility represents a separate embodiment.

In some embodiments, said isolated artificial peptide comprising variant of SEQ ID NO: 1 selected from SEQ ID NO: 8, SEQ ID NO: 9, SEQ ID NO: 11, SEQ ID NO: 12, SEQ ID NO: 15, SEQ ID NO: 17, SEQ ID NO:18, SEQ ID NO: 19, SEQ ID NO: 32 and SEQ ID NO: 35. Each possibility represents a separate embodiment.

In some embodiments, said isolated artificial peptide is consisting of a variant of SEQ ID NO: 1 selected from SEQ ID NO: 8, SEQ ID NO: 9, SEQ ID NO: 11, SEQ ID NO: 12, SEQ ID NO: 15, SEQ ID NO: 17, SEQ ID NO:18, SEQ ID NO: 19, SEQ ID NO: 32 and SEQ ID NO: 35. Each possibility represents a separate embodiment.

In some embodiments, the isolated artificial peptide comprises SEQ ID NO: 1, SEQ ID NO: 8, SEQ ID NO: 17, SEQ ID NO:18, SEQ ID NO: 19, SEQ ID NO: 32 or SEQ ID NO: 35. Each possibility represents a separate embodiment.

In some embodiments, the isolated artificial peptide is consisting of SEQ ID NO: 1, SEQ ID NO: 8, SEQ ID NO: 17, SEQ ID NO:18, 19, SEQ ID NO: 32 or SEQ ID NO: 35. Each possibility represents a separate embodiment.

In some embodiments, the isolated artificial peptide comprises SEQ ID NO: 1. In some embodiments, the isolated artificial peptide comprises SEQ ID NO: 8. In some embodiments, the isolated artificial peptide comprises SEQ ID NO: 9. In some embodiments, the isolated artificial peptide comprises SEQ ID NO: 11. In some embodiments, the isolated artificial peptide comprises SEQ ID NO: 12. In some embodiments, the isolated artificial peptide comprises SEQ ID NO: 15. In some embodiments, the isolated artificial peptide comprises SEQ ID NO: 17. In some embodiments, the isolated artificial peptide comprises SEQ ID NO:18. In some embodiments, the isolated artificial peptide comprises SEQ ID NO: 19. In some embodiments, the isolated artificial peptide comprises SEQ ID NO: 32. In some embodiments, the isolated artificial peptide comprises SEQ ID NO: 35.

In some embodiments, the isolated artificial peptide is consisting of SEQ ID NO: 1. In some embodiments, the isolated artificial peptide is consisting of SEQ ID NO: 8. In some embodiments, the isolated artificial peptide comprises SEQ ID NO: 9. In some embodiments, the isolated artificial peptide is consisting of SEQ ID NO: 11. In some embodiments, the isolated artificial peptide is consisting of SEQ ID NO: 12. In some embodiments, the isolated artificial peptide is consisting of SEQ ID NO: 15. In some embodiments, the isolated artificial peptide is consisting of SEQ ID NO: 17. In some embodiments, the isolated artificial peptide is consisting of SEQ ID NO:18. In some embodiments, the isolated artificial peptide is consisting of SEQ ID NO: 19. In some embodiments, the isolated artificial peptide comprises SEQ ID NO: 32. In some embodiments, the isolated artificial peptide is consisting of SEQ ID NO: 35.

In some embodiments, said isolated peptide is of 10-20 amino acids. In some embodiments, said peptide comprises at least 10 amino acid residues. In some embodiments, said peptide comprises at least 11 amino acid residues. In some embodiments, said peptide comprises at least 12 amino acid residues. In some embodiments, said peptide comprises at least 13 amino acid residues. In some embodiments, said peptide comprises at least 14 amino acid residues. In some embodiments, said peptide comprises less than 20 amino acid residues.

In some embodiments, the isolated peptide is consisting of an amino acid sequence selected from: an amino acid sequence set forth in SEQ ID NO: 23, and an amino acid sequence set forth in SEQ ID NO: 24.

In some embodiments, the isolated peptide is consisting of the sequence set forth in SEQ ID NO: 1, or an analog or derivative thereof.

In some embodiments, the isolated peptide is consisting of the sequence set forth in SEQ ID NO: 23, or an analog or derivative thereof.

In some embodiments, the isolated peptide is consisting of the sequence set forth in SEQ ID NO: 23.

In some embodiments, the isolated peptide is consisting of the sequence set forth in SEQ ID NO: 24, or an analog or derivative thereof.

In some embodiments, the isolated peptide is consisting of the sequence set forth in SEQ ID NO: 24.

In some embodiments, the isolated peptide is fused to a peptide assisting transport through the blood brain barrier (BBB).

In some embodiments, the isolated peptide is a cyclic peptide.

In some embodiments, the amino acid sequence of the isolated peptide further includes therein one or more glycine, alanine and/or cysteine introduced for peptide cyclization.

In some embodiments, the peptide is incorporated into a larger fusion protein in order to increase the stability of the peptide and to assist in delivery thereof to a target cell or tissue. The fusion protein may be designed to incorporate a specific protease cleavage site for recognition by a protease expressed in the target cell or tissue so that the peptide is released from the fusion protein upon entry into the target.

In some embodiments, the peptide is linked to a peptide that favors transport through the blood brain barrier (BBB). For example, the peptide may be fused to ArmaGen Technologies' molecular Trojan horse (MTH). The MTH part of the fusion protein triggers transport across the BBB via an endogenous receptor-mediated transport system.

The isolated peptide disclosed herein can be synthesized using standard protein synthesis techniques as are known in the art, for example using chemical peptide ligation methods, including solid phase peptide synthesis, to synthesize the peptide in the C-terminal to N-terminal direction, including using an automated peptide synthesizer. Alternatively, molecular biology techniques may be used to design an expression cassette that will encode the peptide, using standard molecular biology techniques known in the art. The expression cassette can be used in a suitable expression system. For example, the cassette may be contained in a bacterial plasmid and may be expressed in a bacterial cell, from which the peptide can be isolated and purified, wherein the expression cassette contains an open reading frame encoding the inhibitory peptide, optionally as a complete peptide or as part of a chimeric or fusion peptide or protein, from which the peptide may be released, for example by protease digestion. The expression cassette may also contain suitable regulatory regions operably linked to the open reading frame, for example a promoter region, which may be an inducible promoter region.

In some embodiments, the peptide is included in a biomaterial which increases or induces uptake of the peptide, e.g. by a cell, for example, by encapsulating the peptide in a liposome preparation. Liposome delivery of peptides and proteins to cells is known, and is described, for example, in U.S. Pat. No. 6,372,720 and US 2003/0108597.

In some embodiments, there is provided a pharmaceutical composition comprising an isolated peptide for inhibiting GM-CSF activity and a pharmaceutical acceptable carrier.

In some embodiments, the pharmaceutical composition comprises a peptide having an amino acid sequence selected from the group consisting of: an amino acid sequence set forth in SEQ ID NO: 1, an amino acid sequence set forth in SEQ ID NO: 23, and an amino acid sequence set forth in SEQ ID NO: 24. Each possibility represents a separate embodiment of the present invention.

In some embodiments, the pharmaceutical composition comprises a peptide comprising an amino acid sequence set forth in SEQ ID NO: 1. In some embodiments, the pharmaceutical composition comprises a peptide comprising an amino acid sequence set forth in SEQ ID NO: 23. In some embodiments, the pharmaceutical composition comprises a peptide comprising an amino acid sequence set forth in SEQ ID NO: 24.

In some embodiments, the pharmaceutical composition comprises a peptide consisting of an amino acid sequence set forth in SEQ ID NO: 1. In some embodiments, the pharmaceutical composition comprises a peptide consisting of an amino acid sequence set forth in SEQ ID NO: 23. In some embodiments, the pharmaceutical composition comprises a peptide consisting of an amino acid sequence set forth in SEQ ID NO: 24.

In some embodiments, the pharmaceutical acceptable carrier is selected from the group consisting of: an aqueous solution, vegetable oil, alcohol, polyethylene glycol, propylene glycol or glycerin. Each possibility is a separate embodiment.

In some embodiments, the pharmaceutical composition may further comprise decoy receptor. In some embodiments, decoy GM-CSF may be used. Decoy GM-CSF are GM-CSF molecules that bind to the receptor, but do not activate the receptor, and prevent naturally occurring GM-CSF from binding to the receptors. Decoy GM-CSF molecules may be mutated GM-CSF molecules.

In some embodiments, the pharmaceutical composition may contain pharmaceutically acceptable concentrations of salt, buffering agents, preservatives and various compatible carriers. Each possibility is a separate embodiment. For all forms of delivery, the therapeutic may be formulated in a physiological salt solution. In some embodiments, the pharmaceutical composition may be incorporated in a liposome or other biomaterial useful for protecting and/or preserving the therapeutically active ingredient, e.g. the isolated peptide disclosed herein, until it is delivered to the target cell or tissue. The liposome may also help target the therapeutically active ingredient to a desired location, e.g., a tumor.

In some embodiments, the pharmaceutical composition may further contain one or more additional therapeutic agents useful for inhibiting GM-CSF activity, such as, agents for treating cancer.

In some embodiments, the one or more additional therapeutic agents include inhibitors of hepatocyte growth factor (HGF); inhibitors of monocyte chemotactic protein (MCP1); inhibitors of MCP3 and inhibitors of CXCRL1-CXCR1.

In some embodiments, the pharmaceutical composition further comprises a peptide assisting transport through the blood brain barrier (BBB). In some embodiments, the peptide assisting transport is fused to the isolated peptide for inhibiting GM-CSF activity.

The pharmaceutical composition of the present invention may be prepared by known methods for the preparation of pharmaceutically acceptable compositions suitable for administration to patients, such that an effective quantity of the therapeutic, and any additional active substance or substances, is combined in a mixture with a pharmaceutically acceptable vehicle. On this basis, the pharmaceutical compositions include, albeit not exclusively, solutions of the active ingredients in association with one or more pharmaceutically acceptable vehicles or diluents, and contained in buffer solutions with a suitable pH and iso-osmotic with physiological fluids.

The proportion and identity of a pharmaceutically acceptable diluent used in the pharmaceutical composition is determined by the chosen route of administration, compatibility with live cells, and standard pharmaceutical practice. Generally, a pharmaceutical composition will be formulated with components that will not destroy or significantly impair the biological properties of the active ingredients.

In some embodiments, there is provided a pharmaceutical composition comprising an isolated peptide for inhibiting GM-CSF activity and a pharmaceutical acceptable carrier, for treating glioma.

In some embodiments, there is provided a pharmaceutical composition comprising an isolated peptide for inhibiting GM-CSF activity and a pharmaceutical acceptable carrier, for the preparation of a medicament for treating glioma.

In some embodiments, there is provided a pharmaceutical composition comprising at least one of the isolated peptides disclosed herein and a pharmaceutical acceptable carrier for inhibiting binding of GM-CSF to its receptor.

In some embodiments, there is provided a pharmaceutical composition comprising at least one of the isolated peptides disclosed herein and a pharmaceutical acceptable carrier for inhibiting cellular migration.

According to some embodiments, inhibiting cellular migration comprises preventing or attenuating development of metastasis.

According to some embodiments, inhibiting cellular migration comprises inhibiting invasion of cells through extracellular matrix. According to some embodiments, the cells are tumor cells. According to some embodiments, the tumor is glioma. According to some embodiments, inhibiting cellular invasion comprises preventing spreading of glioma cells via the cerebrospinal fluid to the spinal cord.

In some embodiments, there is provided a pharmaceutical composition comprising an isolated peptide for inhibiting GM-CSF activity and a pharmaceutical acceptable carrier, for use in the treatment of glioma.

In some embodiments, there is provided a method of inhibiting GM-CSF activity in a cell or tissue, e.g., in a human subject, the method comprising exposing the cell or tissue to a therapeutically effective amount of a pharmaceutical composition comprising a peptide comprising an amino acid sequence selected from the group consisting of: an amino acid sequence set forth in SEQ ID NO: 1, an amino acid sequence set forth in SEQ ID NO: 23, and an amino acid sequence set forth in SEQ ID NO: 24, wherein the variants of SEQ ID NO: 1 are selected from SEQ ID NO: 1 with substitution of amino acids in any one or more of positions 2, 3, 5, 6, 9 and 11-13 with alanine or lysine and/or addition of lysine at the N-terminus of SEQ ID NO: 1. Each possibility represents a separate embodiment of the present invention.

In some embodiments, the method comprises administering to a subject in need thereof a therapeutically effective amount of the pharmaceutical composition comprising said peptide.

The term "therapeutically effective amount" as used herein refers to an amount that provides the desired therapeutic result(s), with minimum, or the absence of, adverse side effects sufficient to convince a physician that the potential harm to a patient is greater than the potential benefit to that patient.

Thus, the methods and uses disclosed herein are directed to treating a disease characterized by the presence of a tumor, e.g., a malignant tumor, tumor infiltrated with brain resident (microglia) and peripheral macrophages, having pro-tumoral activity. By way of a non-limiting example, the tumor is a glioma.

In some embodiment, administering a therapeutically effective amount the pharmaceutical composition results in maintenance or reduction of tumor size by at least 10%, 20%, 30%, 40%, 50%, 60%, 70%, 80%, 90% or more. Each possibility represents a separate embodiment of the present invention.

The term "macrophages" s used herein to encompass brain resident (microglia) and peripheral macrophages. Thus, administering to a subject in need thereof a therapeutically effective amount of the pharmaceutical composition disclosed herein may reduce the pro-tumoral activity of the macrophages in the tumor of said subject.

In some embodiments, the pharmaceutical composition is administered locally, e.g., in a tumor, or systemically.

The term "treating" as used herein refers to an approach for obtaining beneficial or desired results, including clinical results. Beneficial or desired clinical results can include, but are not limited to, alleviation or amelioration of one or more symptoms or conditions, diminishment of extent of disease, stabilization of the state of disease, prevention of spread or development of the disease or condition, delay or slowing of disease progression, amelioration or palliation of the disease state, and remission (whether partial or total). "Treating" can also mean prolonging survival of a patient beyond that expected in the absence of treatment. "Treating" can also mean inhibiting the progression of disease, slowing the progression of disease temporarily, although more preferably, it involves halting the progression of the disease permanently.

In some embodiments, the subject in need thereof is a subject in need of treatment or prevention, who is human. The subject may be a subject who has a tumor, such as a subject who has cancer, such as glioma, or a subject likely to develop a glioma Tumors that can be treated according to the methods described herein include tumors that are infiltrated by macrophages having pro-tumoral activity.

The term "pro-tumoral activity" as used herein with respect to macrophages refers to the ability of certain macrophages to contribute to the development of a tumor by, e.g., participation in matrix remodeling, invasion, angiogenesis and suppression of adaptive immunity, rather than initiating anti-tumor responses. Macrophages having pro-tumoral activity are sometimes referred to as having an "M2-like phenotype." Exemplary tumors that contain infiltrating macrophages with pro-tumor activity are brain tumors, such as malignant gliomas. The glioma may be an ependymoma, an astrocytoma (e.g., glioblastoma multiforme), an oligodendroglioma or an oligoastrocytoma. The glioma may be a low-grade glioma or a high-grade glioma. The glioma may also be a supratentorial glioma, an infratentorial glioma or a pontine glioma.

According to some embodiments, the glioma is glioblastoma (GBM).

In some embodiments, the methods described herein further include the step of determining whether a subject has a tumor, such as a malignant tumor. In some embodiments, the methods described herein further include the step of determining whether a subject has a tumor that is infiltrated by macrophages having pro-tumor activity. In some embodiments, the methods described herein further include the step of determining whether a subject has glioma. Once such a determination has been made, the present methods include administering to the subject a therapeutically effective amount of the pharmaceutical composition disclosed herein, thereby stabilizing the tumor or reducing its size.

In some embodiments, the methods described herein include the step of determining whether a subject has a tumor that secretes abnormally high levels of GM-CSF. This may include determining whether the tumor or surrounding environment of the tumor contains more GM-CSF than is found in the same or similar tissue of a healthy subject. The methods may comprise determining whether the subject has a level of serum GM-CSF that is at least 40 pg/ml, at least 50 pg/ml, at least 70 pg/ml, at least 100 pg/ml, at least 200 pg/ml, at least 300 pg/ml, at least 400 pg/ml or at least 500 pg/ml. In some embodiments, the tumor is glioma.

The pharmaceutical composition disclosed herein may be administered to a patient using standard techniques known in the art. The pharmaceutical composition may be administered systemically, or may be administered directly at the site at which a target cell/tissue is located, e.g., the brain.

The pharmaceutical composition may be administered to a patient in a variety of forms depending on the selected route of administration, as will be understood by those skilled in the art. For example, the pharmaceutical composition may be administered topically, surgically or by injection to the desired site. According to some embodiments, a therapeutic is administered topically or by injection (subcutaneously, intravenously, intramuscularly, etc.) directly at the desired site where the target cells are located in the patient.

The concentration and amount of the pharmaceutical composition to be administered vary, depending on the disorder to be treated, the type of therapeutic that is administered, the mode of administration, and the age and health of the patient. However, a person of skill in the art will be able to determine the proper amount.

A variety of methods for determining whether a subject has a tumor that secretes abnormally high levels of GM-CSF may be used, including, but are not limited to, ELISAs or Western Blots, using, e.g., an antibody that bind specifically to GM-CSF. The method may also rely on determining the level, or number, of tumor infiltrating macrophages or microglia cells that have pro-tumor activity. Macrophages or microglia may be isolated and identified based on the cell surface markers that are present on macrophages or micro-glia with pro-tumor activity, but not on those that do not have pro-tumor activity.

Methods for determining the level of GM-CSF may also be based on determining the level of GM-CSF mRNA, e.g., in the tumor cells, instead of, or in addition to, determining the level of the respective proteins.

Methods for determining the level of GM-CSF may include obtaining a tissue sample from a subject. A tissue sample may be a tumor sample, a brain or central nervous system (CNS) sample, e.g., a sample obtained from a glioma tumor. The sample may also be a sample of blood or serum or other bodily fluid.

In some embodiments there is provided a method for determining responsiveness to the pharmaceutical composi-tion disclosed herein, comprising providing a sample of a glioma tumor of a subject and determining the level of macrophages or microglia that have pro-tumor activity in the sample, wherein (i) a lower level of macrophages or microglia that have pro-tumor activity in the sample relative to the level of macrophages or microglia that have pro-tumor activity in the glioma at an earlier time of the treatment with the pharmaceutical composition, or before the beginning of the treatment with the pharmaceutical composition indicates that the treatment has a positive outcome; and (ii) a higher level of macrophages or microglia that have pro-tumor activity in the sample relative to the level of macrophages or microglia that have pro-tumor activity in the glioma at an earlier time of the treatment with the pharmaceutical composition, or before the beginning of the treatment with the pharmaceutical composition indicates that the treatment has a negative outcome.

In some embodiments, there is provided a method for determining the prognosis of a subject having a glioma tumor comprising determining, in a sample from the glioma tumor, the level of macrophages or microglia that have pro-tumor activity, wherein (i) a lower level of macrophages or microglia that have pro-tumor activity relative to their level in the glioma at an earlier time indicates that the treatment has a positive outcome; and (ii) a higher level of macrophages or microglia that have pro-tumor activity relative to their level at an earlier time indicates that the prognosis is not favorable.

In some embodiments, the level of macrophages or micro-glia that have pro-tumor activity is compared to a control value. A control value may be a value that is the average (e.g., statistically significant) of the level of macrophages or microglia that have pro-tumor activity in subject who were found to have a good prognostic.

In some embodiments there is provided a method for determining the prognosis of a subject having a tumor, e.g., a glioma, comprising providing a sample of the subject having the tumor, and determining the level of GM-CSF in the sample, wherein (i) a higher level of GM-CSF in the sample of the subject having a tumor relative to the level in a subject that does not have a tumor indicates that the subject has a poor prognosis; and (ii) a lower or similar level of GM-CSF in the sample of the subject having a tumor relative to the level in a subject that does not have a tumor indicates that the subject has a good prognosis.

The sample may be a brain sample, a tumor sample, a sample of tissue or fluid in the vicinity of the tumor (e.g., intracranial fluid), or blood or serum sample. The tumor may be a glioma, e.g., glioma multiforme. The method may comprise determining the level of GM-CSF protein or the level of GM-CSF nucleic acid, e.g., RNA, such as mRNA. Typically, the level of GM-CSF protein is undetectable in healthy subjects; and a level of GM-CSF equal to or above 40 pg/ml indicates an abnormal condition, e.g., the presence of a tumor. Accordingly, the level of GM-CSF in a subject that does not have a tumor is usually less than 40 pg/ml (Rafat et al., J Neurosurg., 112: 43-49, 2010).

It is to be understood that the level of GM-CSF is up-regulated 3 to 5 folds in low grade gliomas and more than 200 fold in high grade gliomas. Accordingly, also provided herein is a method for determining the prognosis (or severity of disease) of a subject having a tumor, e.g., a glioma, comprising providing a sample of the subject having the tumor, and determining the level of GM-CSF in the sample, wherein (i) a level of GM-CSF in the sample of the subject having a tumor that is at least 100 fold, 150 fold, or 200 fold higher relative to the level in a subject who does not have a tumor indicates that the subject has a poor prognosis; and (ii) a level of GM-CSF in the sample of the subject having a tumor that is similar to or lower than the level in a subject who does not have a tumor indicates that the subject has a good prognosis.

In some embodiments, the tumor is glioma and a level of GM-CSF in the serum sample of the subject having a tumor that is higher than 100 pg/ml, 150 pg/ml, 200 pg/ml, 300 pg/ml, 400 pg/ml, or 500 pg/ml indicates that the subject has a poor prognosis.

In some embodiments, the tumor is glioma and a level of GM-CSF in the serum sample of the subject having a tumor that is lower than 100 pg/ml, 150 pg/ml, 200 pg/ml, 300 pg/ml, 400 pg/ml, or 500 pg/ml indicates that the subject has a good prognosis In some embodiments, poor prognosis corresponds to an aggressive tumor, e.g., a high grade glioma.

In some embodiments, poor prognosis corresponds to a non-aggressive tumor e.g., a low grade glioma.

In some embodiments, a level of GM-CSF that is lower than a control value indicates that the prognosis of the subject is favorable, whereas a level of GM-CSF that is higher than a control value indicates that the prognosis is not favorable. The control value may be a value that is the average (e.g., statistically significant) of the level in subject who were found to have a good prognosis, e.g., a glioma that has stabilized, regressed or is progressing only slowly rela-tive to other gliomas. The control value for GM-CSF levels may be 50 pg/ml, 40 pg/ml, or 15 pg/mL. Each possibility represents a separate embodiment of the present invention.

In some embodiments, determining the level of GM-CSF comprises determining the activity of GM-CSF in the sample.

Also provided are methods for identifying a subject who may be treated as described herein, e.g., by administration of a GM-CSF inhibitor. Methods for identifying such subjects may include obtaining a sample from the subject, e.g., a brain sample, such as a brain tumor sample or sample of intracranial fluid, or a blood or serum sample, and deter-mining the level of GM-CSF protein or activity (e.g., activity can be determined) in the sample, wherein the presence of a level or activity of GM-CSF in the sample that is higher than a control value indicates that the subject can be treated by the administration of a GM-CSF inhibitor, whereas a level or activity of GM-CSF in the sample that is lower than a control value indicates that the subject will not likely be responsive to a treatment with a GM-CSF inhibitor. The control value may be the median or average (statistically significant) level or activity of GM-CSF in subjects who do not have a brain tumor, e.g., subjects who do not have glioma. For example, a control value, e.g., in a serum sample, may be 40 pg/ml or 100 pg/ml. Thus, e.g., a subject having a blood or serum level of GM-CSF that is higher than 40 pg/ml, 100 pg/ml, 250 pg/ml, 300 pg/ml, 400 pg/ml or 500 pg/ml can be treated by the administration of a GM-CSF inhibitor, whereas a subject having a blood or serum level of GM-CSF that is lower than 100 pg/ml or 40 pg/ml may not be responsive to a treatment with a GM-CSF inhibitor.

The method for determining whether a subject is likely to respond to a treatment with a GM-CSF inhibitor may also comprise administering to the subject (e.g., a single dose of) a GM-CSF inhibitor; obtaining a tumor sample from the subject and determining the level of invading macrophages/microglia, wherein a lower level of invading macrophages/microglia in the tumor sample of the subject relative to the level of invading macrophages/microglia in the tumor prior to the administration of the GM-CSF inhibitor indicates that the subject is likely to respond to a treatment with a GM-CSF inhibitor, whereas a similar or higher level of invading macrophages/microglia in the tumor sample of the subject relative to the level of invading macrophages/microglia in the tumor prior to the administration of the GM-CSF inhibitor indicates that the subject is not likely to respond to a treatment with a GM-CSF inhibitor. A method may comprise obtaining a tumor sample prior to administration of the GM-CSF inhibitor.

Further provided are diagnostic methods for determining the presence of a tumor producing GM-CSF, such as an aggressive glioma. The method may comprise providing a sample of a subject, such as a brain sample or a tumor sample or serum sample, and determining the level or activity of GM-CSF. The presence or activity of GM-CSF that is at least 100 fold, 150 fold, 200 fold, 250 fold, 300 fold, 400 fold or 500 fold higher than that in a subject who does not have glioma, indicates the presence of a tumor and a poor prognosis.

It is also possible to measure levels of GM-CSF within the body of a subject, using non-invasive procedures, e.g., imaging technologies for detecting GM-CSF. In such instances, it is not necessary to obtain a sample from the subject.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXAMPLES

Example 1: CSF2 Expression is Up-Regulated in GBM

Transcriptomic analyses of hundreds of glioma samples deposited in TCGA (the Cancer Genome Atlas) indicate up-regulation of CSF2 (a gene coding for GM-CSF) in a subset of GBM, mainly in the mesenchymal subtype (FIGS. 1A-1E).

Figure 1A:
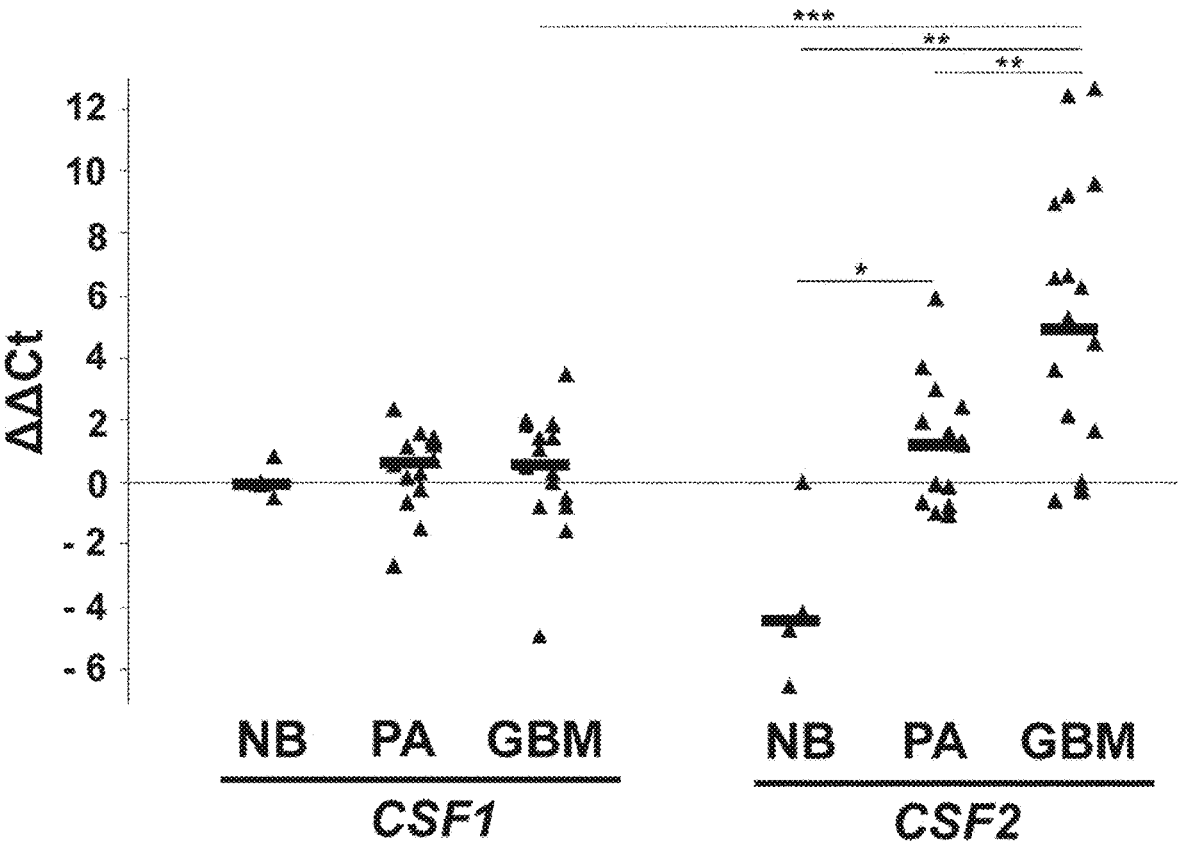
FIG. 1A presents expression of CSF1 and CSF2 genes in glioma (GBM), pilocytic astrocytoma (PA) and normal (NB) tissue brain samples deposited in TCGA.
Figure 1B:
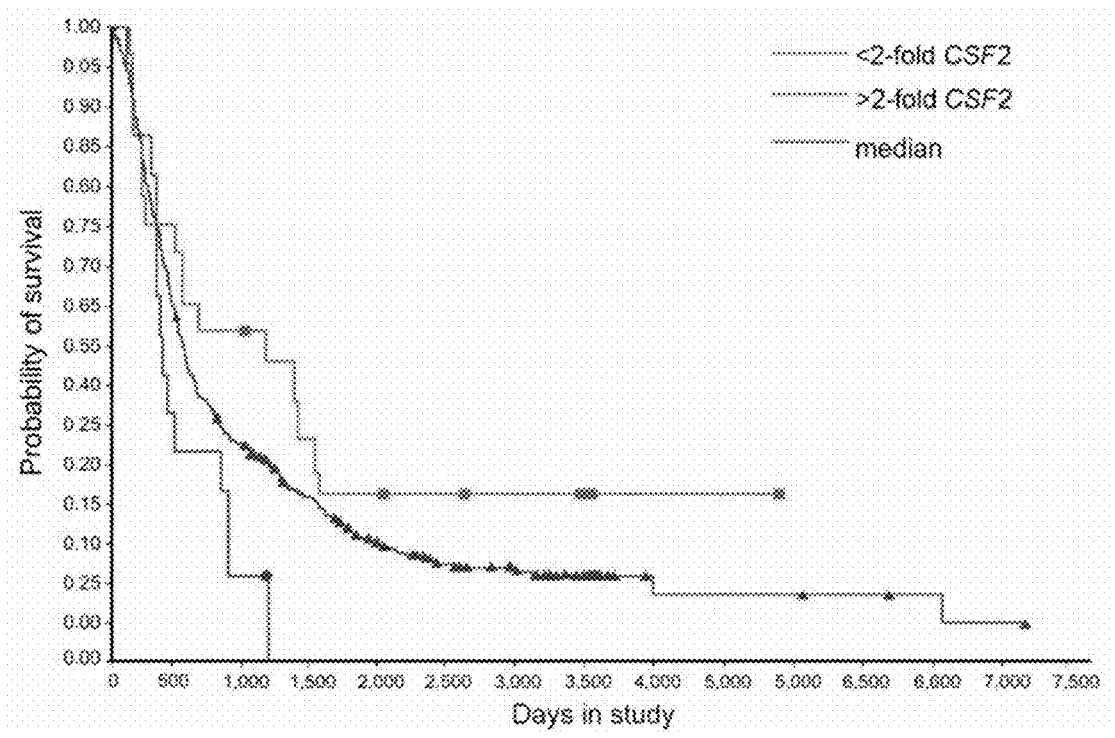
FIG. 1B presents expression of CSF2 gene as a function of patients' survival, obtained from Rembrandt database
Figure 1C:
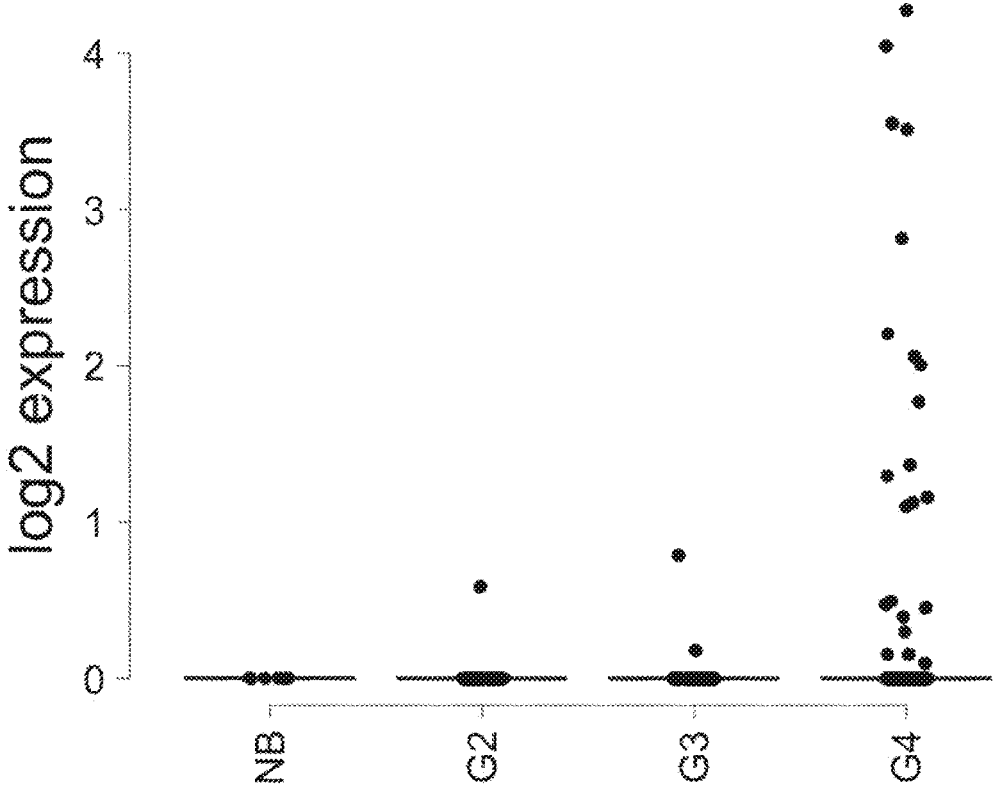
FIG. 1C presents expression of CSF2 gene in normal brain (NB), low grade glioma (G2) and high-grade glioma (G3, G4) samples obtained from TCGA database
Figure 1D:
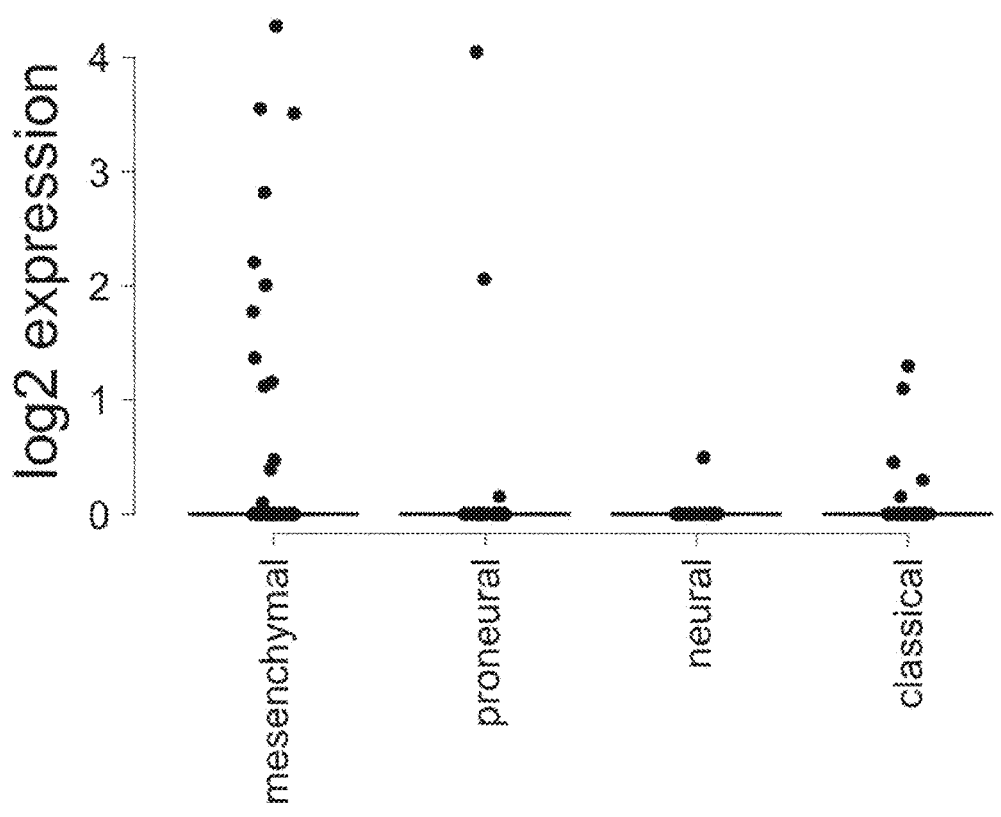
FIG. 1D presents expression of CSF2 gene in samples of mesenchymal, proneural, neural and classical GBM tissue samples obtained from TCGA database

The data shows that CSF1 and CSF2 in pilocytic astrocytoma (PA, benign glioma) and Glioblastoma (GBM) relate to their levels in normal brains where only CSF2 is significantly upregulated in GBMs (FIG. 1A). CSF2 is not expressed in the normal brain (FIG. 1A). The analysis of the REMBRANDT database shows inverse correlation of CSF2 mRNA levels with patient's survival (FIG. 1B). The analysis of TCGA datasets show upregulation of CSF2 mRNA in mesenchymal GBMs and correlation with an inflammatory, preinvasive milieu (FIG. 1D).

Thus, the levels of CSF2 mRNA in glioma cell lines are up-regulated in comparison to normal human astrocytes. Stable knockdown of CSF-2 in human LN18 and U87 glioma cells reduced intracranial glioma growth in nude mice, inhibited pro-tumorigenic accumulation and polarization of microglia/macrophages and extended animal survival (data not shown).

Figure 1E:
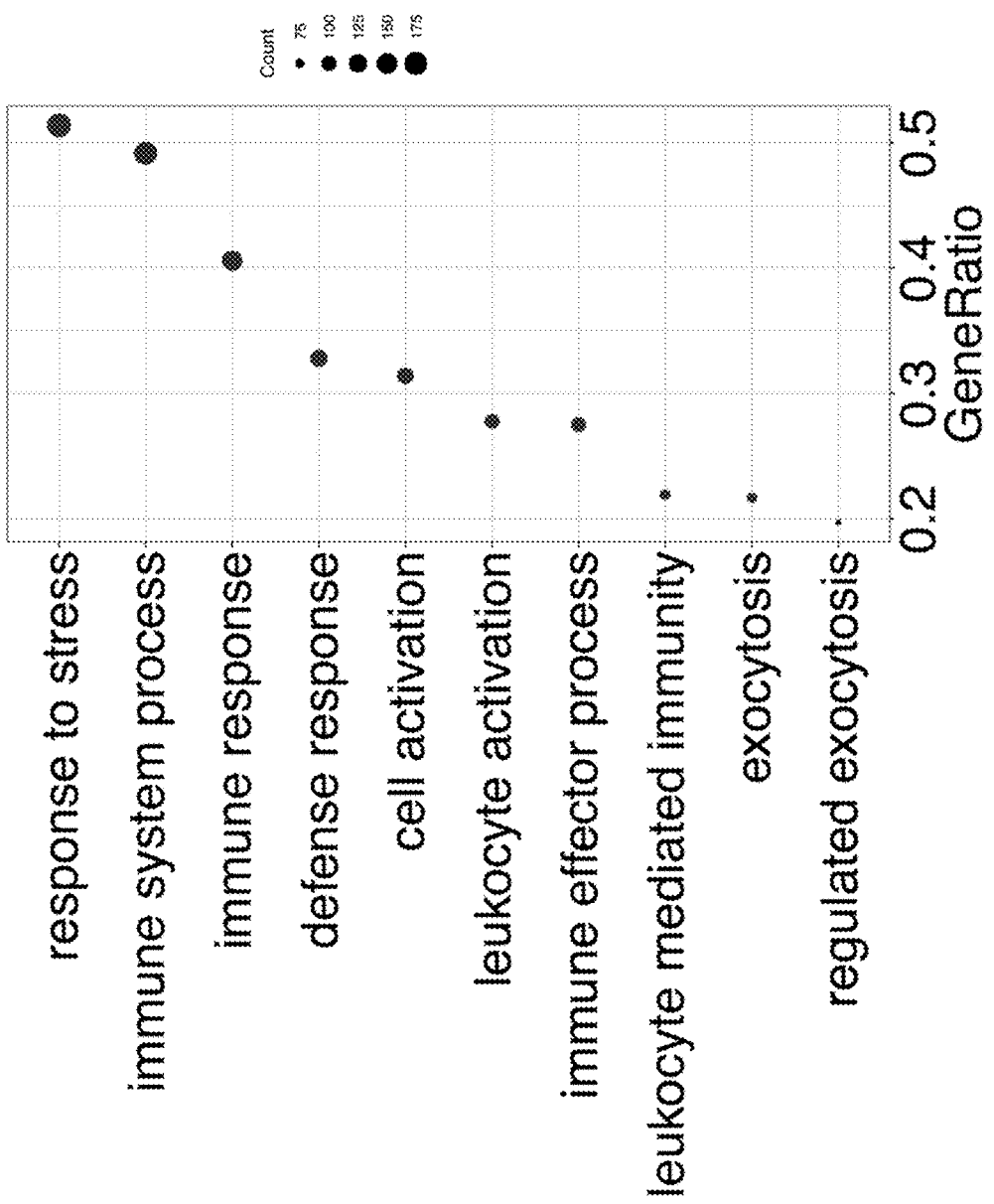
FIG. 1E presents groups of genes related to particular processes which were significantly enriched (adjusted p-value<0.01) in gliomas with high CSF2 expression.

GBM patients with high CSF2 expression have significantly upregulated expression of immune/invasion genes (FIG. 1E).

Example 2: Design, Identification and Selection of Specific Interacting Peptides GM-CSF binds to GM-CSFR receptor that consists of a unique ligand-binding alpha chain and a common beta chain. GM-CSFR alpha subunit is specific for binding GM-CSF, where the beta subunit is also involved in the interaction with other cytokines (IL-3 and IL-5). Based on the crystal structures of GM-CSF in complex with its receptors, the receptor regions involved in the interactions were determined. Based on the human protein sequence of GM-CSFR, 26 peptides were designed, each 14-residues long, with an offset of 7 amino acids.

To identify the best interacting peptides three different methods were applied: peptide microarrays, enzyme-linked immunosorbent assay (ELISA) and a technique based on surface plasmon resonance (SPR). To perform these experiments recombinant human GM-CSF protein was required. To this end, cDNA encoding human GM-CSF was cloned into an expression vector designed to produce Myc-tagged/His-tagged proteins and effective isolation of high purity recombinant protein produced by mammalian cells was achieved. Protein purity was evaluated in SDS-PAGE followed by Coomassie staining.

Figure 2A:
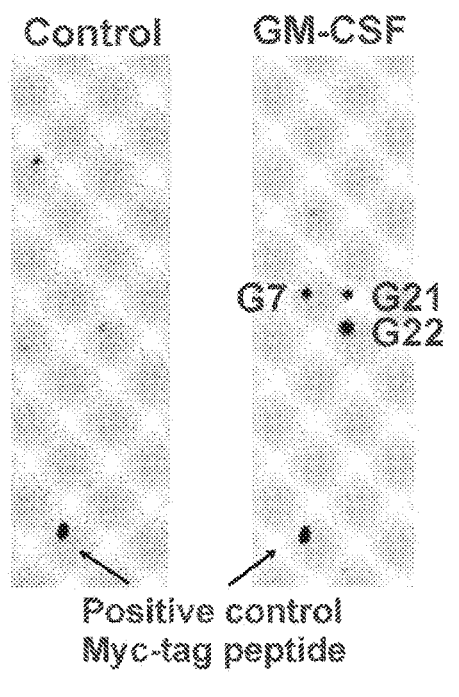
FIG. 2A presents peptides interacting with GM-CSF identified using peptide microarrays and anti-Myc immunostaining. The control peptide containing Myc-tag and the peptides bound with Myc-tagged GM-CSF are marked on the images.

The peptide library was printed on glass surfaces (JPT Peptide Technologies, GmbH). Microarrays were incubated with: a buffer (control—without protein), or a recombinant human GM-CSF protein, unbound proteins were removed by several washing steps, then the arrays were blocked with 5% milk solution. Binding was detected using anti-Myc antibody recognizing the Myc-tag of GM-CSF, followed by a secondary, anti-rabbit antibody conjugated with a fluorescent dye—Dylight800. To monitor the accuracy of detection of the Myc-tag using a positive control peptide GSGEQK-LISEEDLN (SEQ ID NO: 2) containing this tag was spotted on the array. Peptide GSGSGSGSGHHHHHH (SEQ ID NO: 3), which was not derived from GM-CSFR, was used as a negative control. In the control microarray, incubated without the protein, only the signal from positive control peptides was detected. GM-CSF bound 3 peptides: G7 (SEQ ID NO: 1), G21 (SEQ ID NO: 30) and G22 (SEQ ID NO: 31; FIG. 2A; Table 1 and FIG. 8B).

TABLE 1

| Peptide | Sequence (AA) | Seq. ID No. |
| --- | --- | --- |
| G7 | YQKLSYLDFQYQLD | 1 |
| +ive control | GSGEQKLISEEDLN | 2 |
| -ive control | GSGSGSGSGHHHHHH | 3 |
| G7 N-terminal | YQKLSYL | 4 |
| G7 C-terminal | DFQYQLD | 5 |
| G7 central portion | LSYLDFQ | 6 |
| G7 variant (A1) | AQKLSYLDFQYQLD | 7 |
| G7 variant (A2) | YAKLSYLDFQYQLD | 8 |
| G7 variant (A3) | YQALSYLDFQYQLD | 9 |
| G7 variant (A4) | YQKASYLDFQYQLD | 10 |
| G7 variant (A5) | YQKLAYLDFQYQLD | 11 |
| G7 variant (A6) | YQKLSALDFQYQLD | 12 |
| G7 variant (A7) | YQKLSYADFQYQLD | 13 |
| G7 variant (A8) | YQKLSYLAFQYQLD | 14 |
| G7 variant (A9) | YQKLSYLDAQYQLD | 15 |
| G7 variant (A10) | YQKLSYLDFAYQLD | 16 |
| G7 variant (A11) | YQKLSYLDFQAQLD | 17 |
| G7 variant (A12) | YQKLSYLDFQYALD | 18 |
| G7 variant (A13) | YQKLSYLDFQYQAD | 19 |
| G7 variant (A14) | YQKLSYLDFQYQLA | 20 |
| G7 variant (A15) | YQKLSYLDFQYQLDVHRKN | 21 |
| G7 variant (A16) | KQPRTYQKLSYLDFQYQLD | 22 |
| G5 | NTTHCLVRWKQPRT | 23 |
| G25 | NHEVEDEIIWEEFT | 24 |
| G3 | IERFNPPSNVTVRC | 25 |
| G6 | RWKQPRTYQKLSYL | 26 |
| G14 | HSVKIRAADVRILN | 27 |
| G15 | ADVRILNWSSWSEA | 28 |
| G16 | WSSWSEAIEFGSDD | 29 |
| G21 | VLGFLFKRFLRIQR | 30 |
| G22 | RFLRIQRLFPPVPQ | 31 |

Figure 2B:
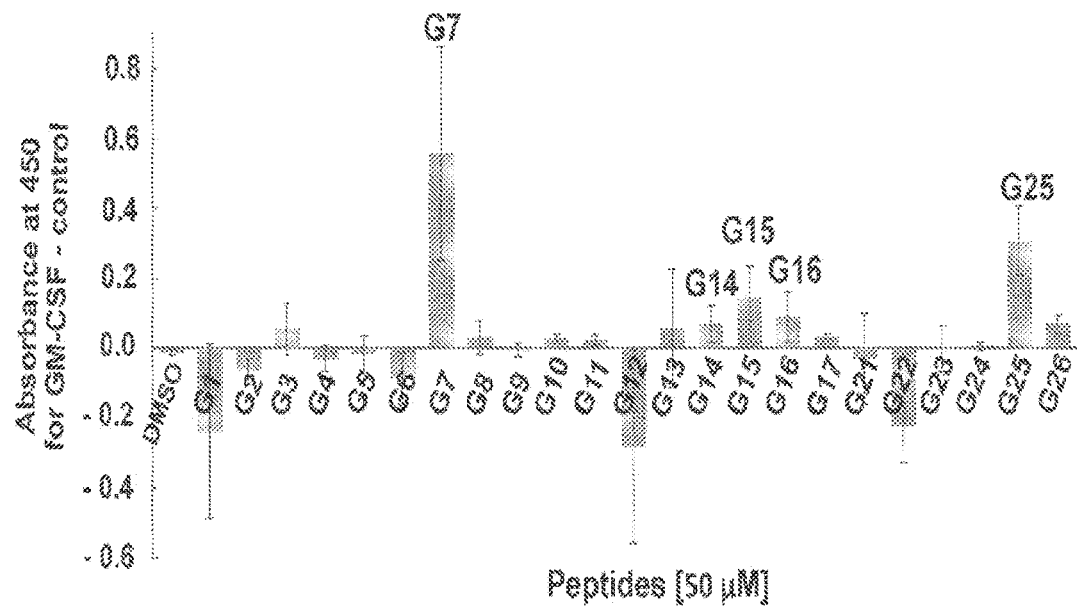
FIG. 2B presents peptides interacting with GM-CSF, identified using ELISA.

The results obtained using peptide microarrays were verified by an ELISA test. The ELISA 96-well plates were coated with a recombinant GM-CSF; non-coated wells were used as a control. Next, unbound proteins were washed out, then the wells were blocked with 5% BSA (bovine serum albumin) in saline and peptides labeled with N-terminal biotin (purchased from GenScript) were added. Subsequently, peptides that bound GM-CSF were detected using an anti-biotin antibody, followed by a secondary antibody conjugated to horseradish peroxidase (HRP). HRP catalyzes the conversion of chromogenic substrates into colored products. The amount of bound peptide was proportional to the amount of the colored product, and it was measured using a spectrophotometer. As shown in FIG. 2B, six (6) peptides strongly interacting with GM-CSF were identified: G3 (SEQ ID NO: 25), G7 (SEQ ID NO:1), G14 (SEQ ID NO: 27), G15 (SEQ ID NO: 28), G16 (SEQ ID NO: 29) and G25 (SEQ ID NO: 24).

Figure 2C:
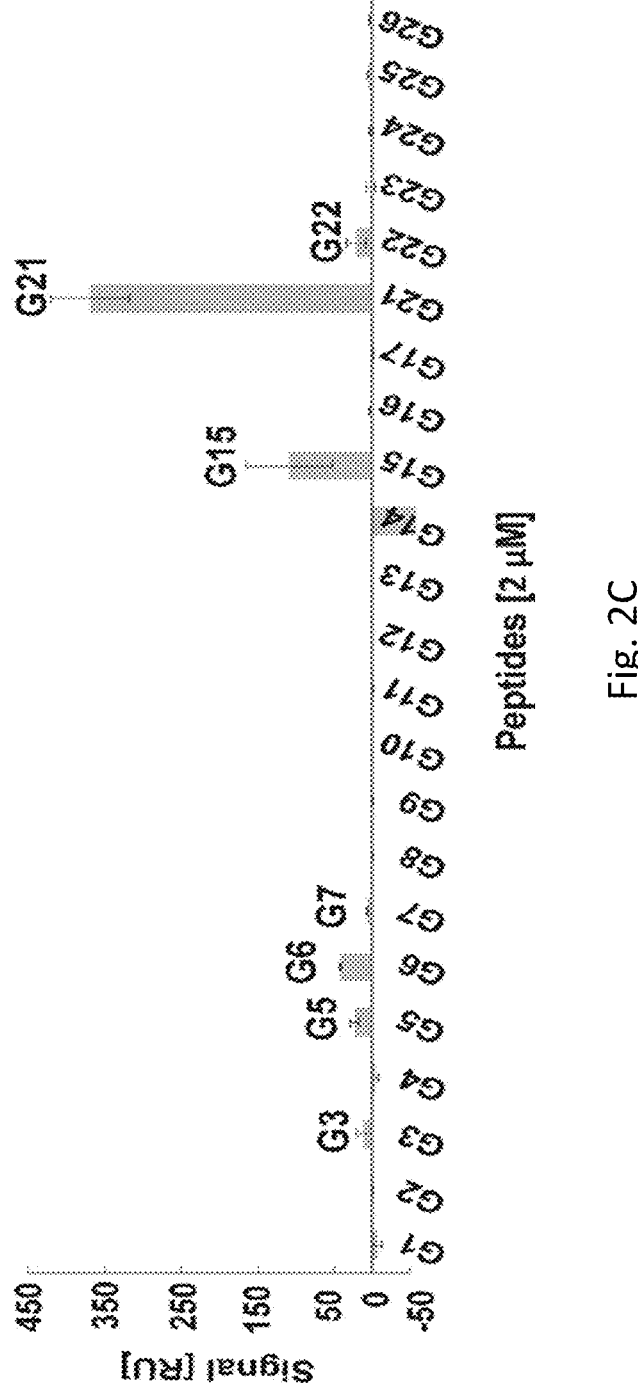
FIG. 2C presents peptides interacting with GM-CSF, identified by SPR (surface plasmon resonance).

To further confirm specificity of detected interactions, the strength of direct interaction between GM-CSF and peptides was measured using a method based on surface plasmon resonance (BIAcore 3000 instrument, GE Healthcare). GM-CSF was immobilized on a chip and G-peptides were injected. Seven GM-CSF binding peptides were identified: G3 (SEQ ID NO: 25), G5 (SEQ ID NO: 23), G6 (SEQ ID NO: 26), G7 (SEQ ID NO:1), G15 (SEQ ID NO: 28), G16 (SEQ ID NO: 29), G21 (SEQ ID NO: 30) and G22 (SEQ ID NO: 31; FIG. 2C). These peptides encompass peptides identified by ELISA and microarrays that confirmed the reliability of the results obtained by these two methods. Thus, further analyses were carried out with all the peptides identified as interacting with GM-CSF: G5 (SEQ ID NO: 23), G6 (SEQ ID NO: 26), G7 (SEQ ID NO:1), G14, G15, G16, G21, G22 (SEQ ID NOs: 27-31, respectively) and G25 (SEQ ID NO: 24).

Example 3: Cytotoxicity Evaluation

Figure 3A:
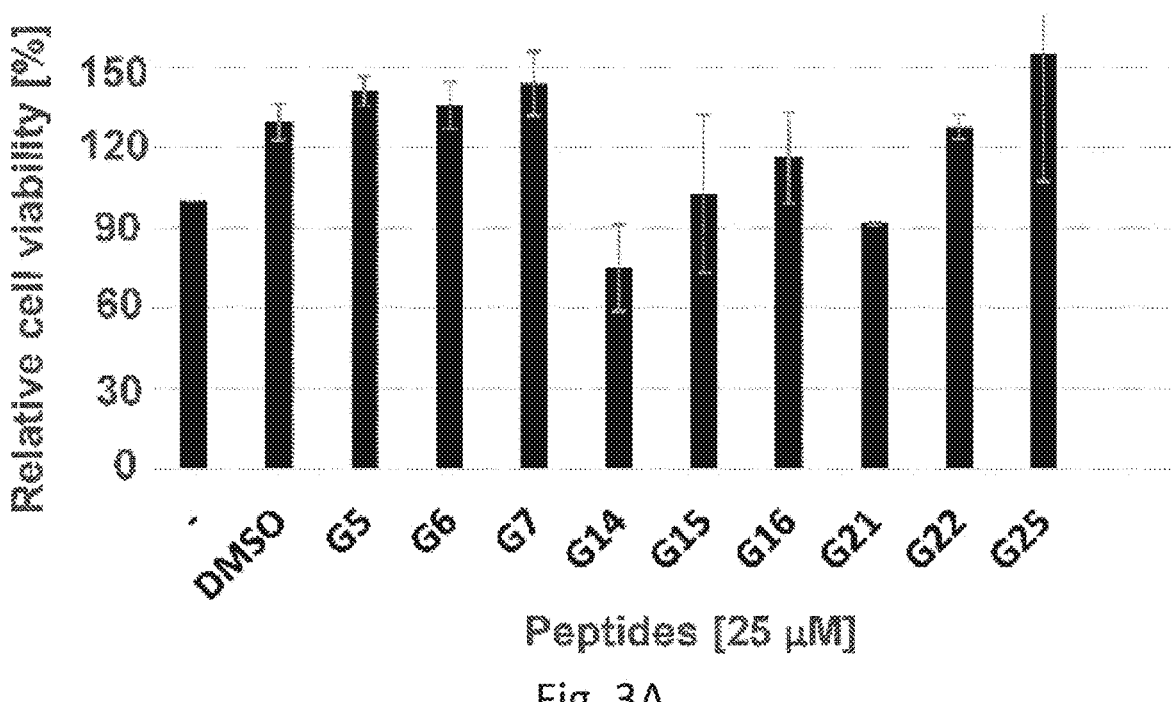
FIGS. 3A to 3D present the cytotoxic effect of the peptides disclosed herein, at concentrations of 25 μM (FIGS. 3A, 3C) or μM 100 (FIGS. 3B, 3D) on relative cell viability (relative to untreated cells set as 100%). Each value reflects three independent experiments and is presented as means +/−s.d. (standard deviations, error bars).
Figure 3B:
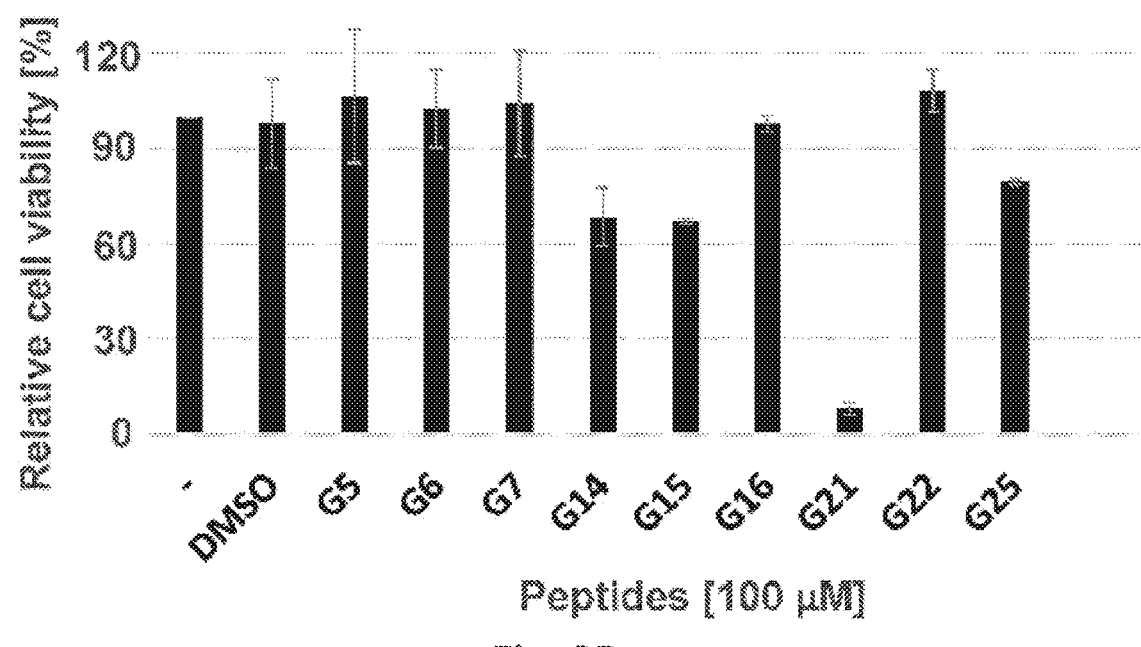
Figure 3C:
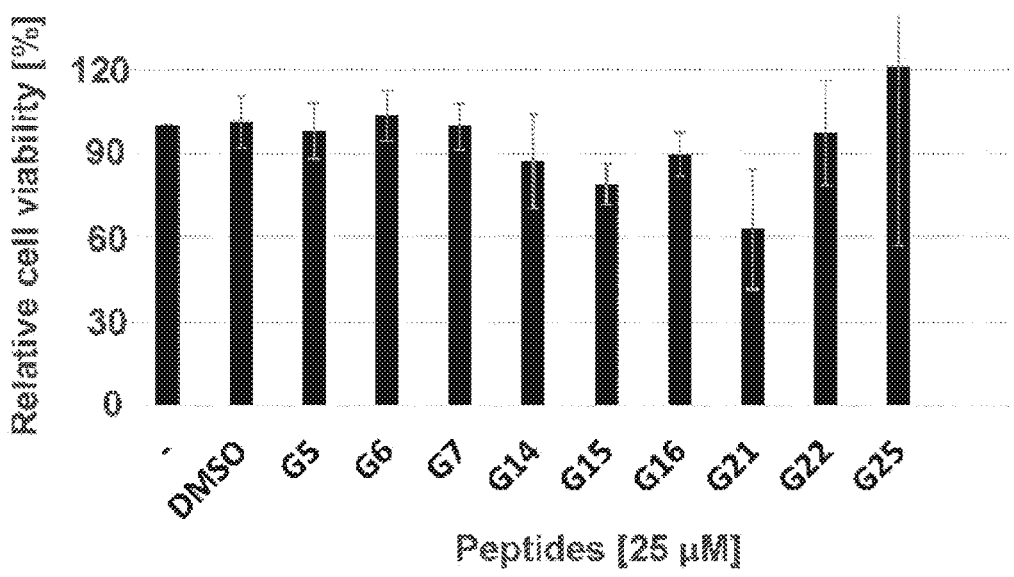
Figure 3D:
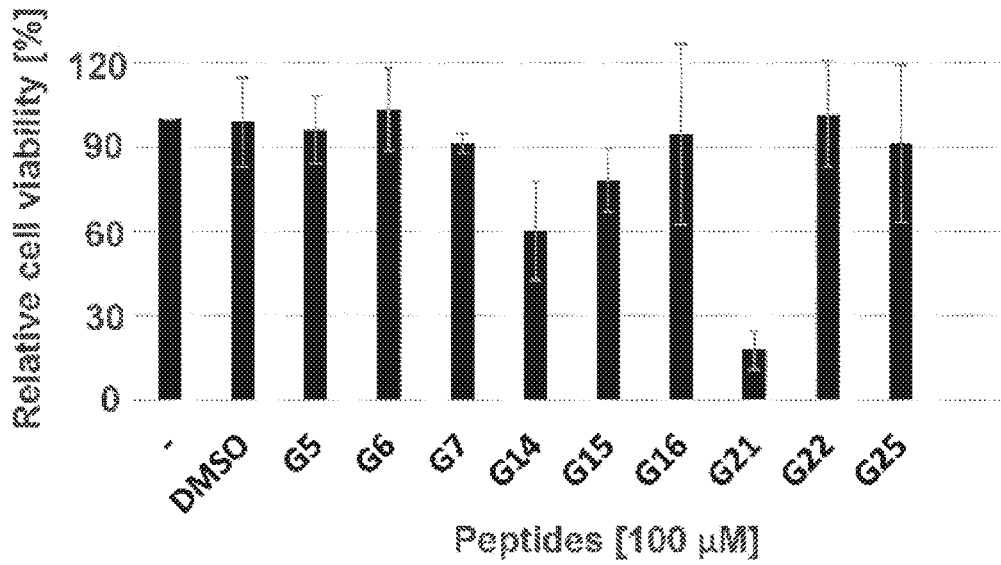

To exclude potential cytotoxic peptides, the influence of the selected peptides was analyzed on BV2 microglial cells (FIGS. 3A and 3B) or U87 MG glioma cells (FIGS. 3C and 3D). Cell viability of each cell type was determined after treatment at various concentrations of the tested peptides. Cell viability was determined using MTT metabolism test (colorimetric assay). In this test, mitochondrial dehydrogenase catalyzes the reduction of tetrazolium salt (MTT) into an insoluble formazan, which has a purple color. The amount of the reduced MTT is proportional to the number of living, metabolically active cells and can be measured by a spectrophotometer. The effects of the peptides on survival of murine microglial BV2 cells (an immortalized murine microglial cell line) and human glioma U87 MG cells (ATTC), was measured. Cells were seeded on plates in standard cell culture media and treated for 18 h with peptides at two concentrations 25 μM (FIGS. 3A and 3C) and 100 μM (FIGS. 3B and 3D). Cell viability of untreated cells, was set as 100%. Peptides that produced cytotoxic effects on BV2 (FIGS. 3A and 3B) and U87 MG cells (FIGS. 3C and 3D), namely, reduced cell viability by 30%-80% in comparison to untreated cells, were excluded from further analyses (G14, G15, G21 (SEQ ID NOs: 27, 28 and 30, respectively; see FIGS. 3A-3D).

Example 4: Blocking Microglia-Dependent Invasion of Glioma Cells

Figure 4A:
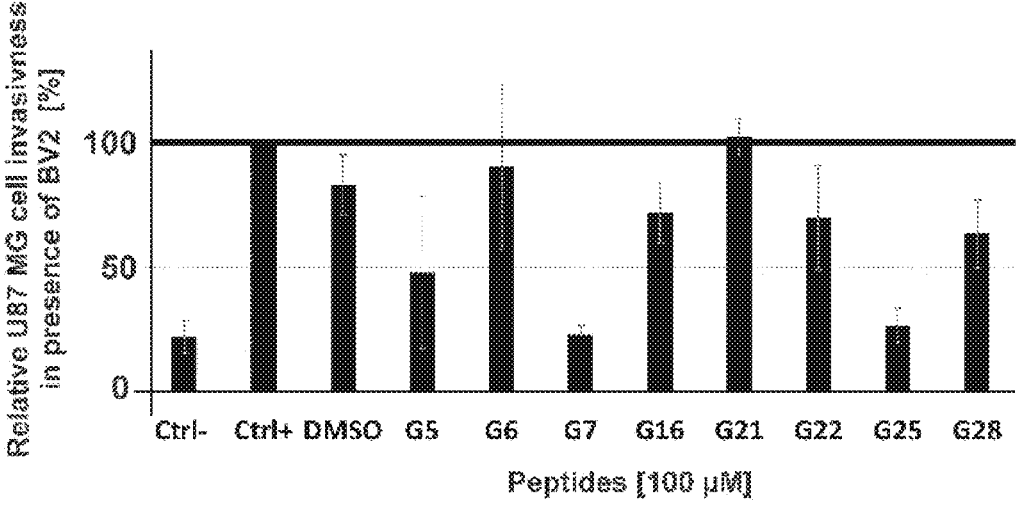
FIG. 4A presents the influence of GM-CSF-binding peptides (G-peptides) on glioma cell invasion induced by the presence of microglia BV2 cells measured using Matrigel assay.
Figure 4B:
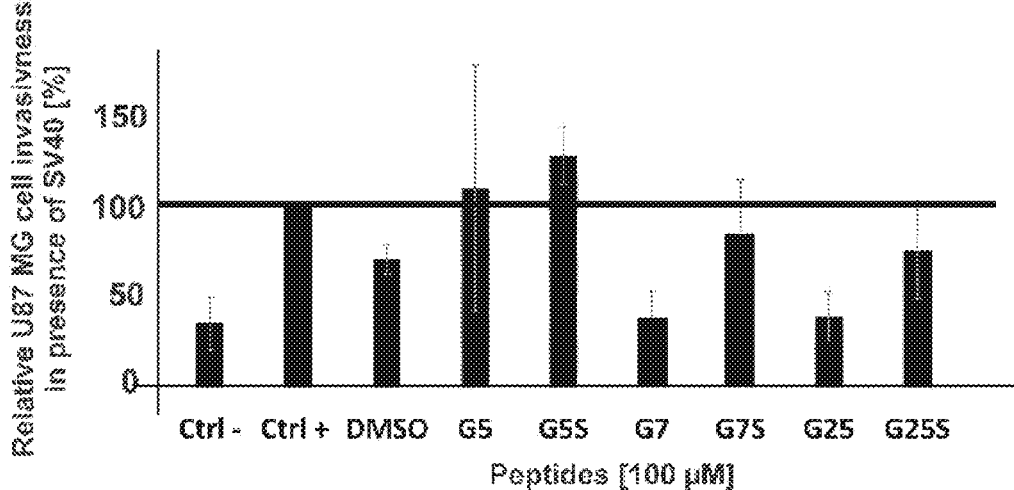
FIG. 4B presents the impact of selected G-peptides (G5, G7, G25; SEQ ID NOs: 23, 1 and 24, respectively) and control peptides (scrambled peptides, referred as S) on the invasion of U87 MG cells in the presence of SV40 cells.
Figure 4C:
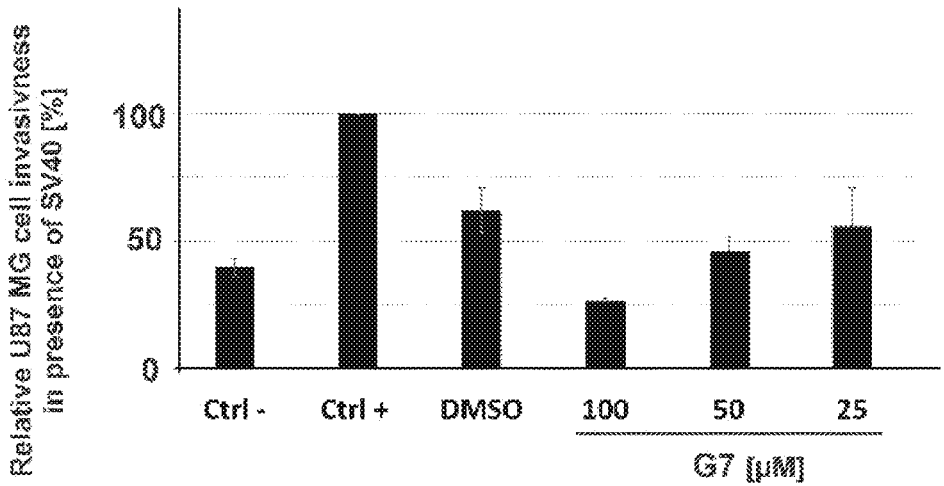
FIG. 4C presents dose dependent effect of G7peptide (SEQ ID NO: 1) on U87 MG invasion induced by human SV40 microglial cells.
Figure 4D:
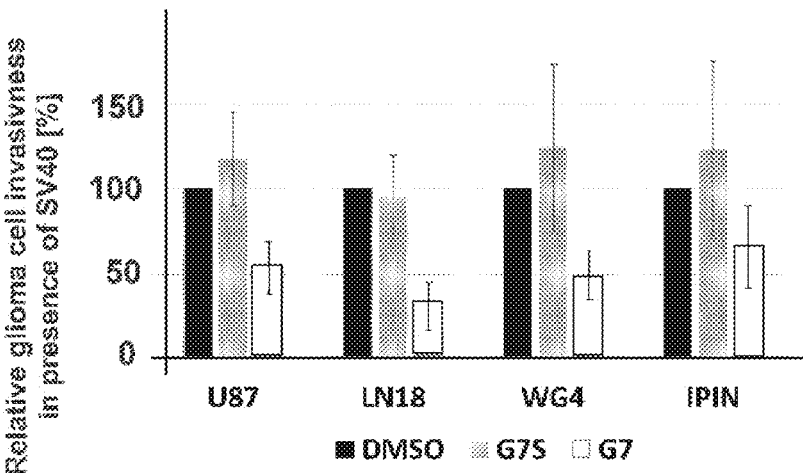
FIG. 4D presents the impact of G7 peptide (SEQ ID NO: 1; white bars) and control peptides (scrambled peptides, referred as G7S; gray bars) on the invasion of different human glioma cells in presence of SV40 microglia cells: WG4 and IPIN patient-derived glioma cell cultures; Ctrl⁻.

Blockade of tumor cell invasion by peptides was analyzed in microglia-glioma co-cultures using a Matrigel assay as described (Sliwa et al. 2007, ibid; Wesolowska et al. 2008, ibid). In this method, invasion chambers with 8 μM pores were coated with Matrigel Matrix, serving as a reconstituted extracellular matrix, which is digested by invading tumor cells. Human glioma cells poorly invade the matrigel unless co-cultured with microglia (FIGS. 4A-4C). The invasion of U87 MG glioma cells was measured in the absence or presence of either murine BV2 microglial cells (FIG. 4A) and or human microglial cells (SV40-tranformed microglia; Applied Biological Materials Inc.; FIGS. 4B-4D). Peptides were added to upper and lower chambers in media with 2% serum. After 18 h, cells were fixed on the insert membranes, cell nuclei were stained with a fluorescent dye (DAPI) and microphotographs of the invading cells from five randomly selected fields per insert were taken (center and four corners). A total number of invading cells was counted using ImageJ®. The presence of microglial cells doubled glioma invasion (FIGS. 4A-4C). G7 (SEQ ID NO: 1), G5 (SEQ ID NO: 23), and G25 (SEQ ID NO: 24) peptides reduced the invasiveness of U87 MG cells in the presence of BV2 cells (FIG. 4A). Additionally, peptides G7 (SEQ ID NO: 1) and G25 (SEQ ID NO: 24) inhibited invasiveness of U87 MG cells in the presence of SV40-human microglial cells (FIG. 4B). Control, scrambled peptides, G7S and G25S had no effect on tumor invasiveness (FIG. 4B). G7 peptide (SEQ ID NO: 1) reduced the invasiveness of U87 MG cells to the control level (FIGS. 4A-4C), and therefore was selected for further analysis. The effect of G7 peptide (SEQ ID NO: 1) on invasion was concentration dependent (FIG. 4C). Additionally, G7 (SEQ ID NO: 1) reduced the invasion of other human glioma cells: LN18 cell line and primary cultures of WG4 and IPIN cells obtained from surgical GBM specimens (FIG. 4D).

Example 5: G7 Peptide Blocks Binding of GM-CSF and GM-CSFR Alpha Subunit

To verify the mechanism of G7 peptide action, its effect on binding between GM-CSF and GM-CSFR alpha subunit was analyzed by SPR using BIAcore 3000 instrument (GE Healthcare). GM-CSFR alpha was immobilized on a chip and GM-CSF (FIG. 5A) or GM-CSF with G7 peptide (SEQ ID NO: 1) in a 1:5 ratio (FIG. 5B) were injected at increasing concentrations (0.5-8.0 µM). GM-CSFR alpha was immobilized on the second cell of the chip, the first cell was a control where no protein was immobilized thereon. In order to verify that the solvent (100% DMSO) used for dissolving the peptide does not influence the binding DMSO was mixed with GM-CSF in the same proportion as GM-CSF and G7 (SEQ ID NO: 1) and injected on the chip. DMSO did not disrupt the interaction. Signals obtained from controls were subtracted. The binding curves were analyzed by BIA evaluation software. RU values were increasing proportionally to GM-CSF concentrations. The addition of the G7 peptide (SEQ ID NO: 1) fully blocked binding of GM-CSF to its receptor—GM-CSFR alpha.

Example 6: G7 Peptide Inhibits Binding of GM-CSF to its Receptor In Vivo

To verify the influence of G7 peptide (SEQ ID NO: 1) on the binding of GM-CSF to its receptor in living cells, analysis was performed using LigandTracer®, an instrument that enables measuring protein-living cells interaction in real time. To this end, the binding of GM-CSF labeled with fluorescein (FITC) to human monocytic U937 cells was analyzed. U937 cells were periodically flushed with medium containing GM-CSF alone or GM-CSF with either G7 (SEQ ID NO: 1) or G7S (a scrambled control peptide) and the fluorescence signals, corresponding to the amount of protein bound to the cells, was measured (FIG. 6A).

The results indicate that G7 peptide (SEQ ID NO: 1) inhibits the interaction between GM-CSF and its receptor on U937 cells in a concentration dependent manner (FIG. 6B).

Example 7: The Influence of G7 Peptide on Intracellular Signaling

The influence of G7 peptide (SEQ ID NO: 1) on the signaling pathway induced by GM-CSF was tested in immune system cells: human monocytic U937 cells. After binding to its receptor, GM-CSF induces JAK-STAT signaling cascade and one of the steps of this pathway is the phosphorylation of the transcription factor STAT5. Human monocytic U937 cells were stimulated for 30 min with conditioned medium from glioma LN18 cells (GCM LN18). Next, U937 cell lysates were analyzed using Western blot technique and an antibody which recognizes the phosphorylated form of STAT5 (p-STAT5). Incubation of U937 cells with LN18 GCM induced phosphorylation of STAT5 (FIG. 7). GCM-induced phosphorylation of STAT5 was inhibited in the presence (upon addition of) G7 peptide (SEQ ID NO: 1).

Example 8: Identification of G7 Residues Crucial for its Activity

G7 peptide encompasses amino acid sequence YQKL-SYLDFQYQLD (SEQ ID NO: 1). In order to identify the minimal sequence of G7 essential for GM-CSF binding 3 peptides were designed, consisting of parts of G7 peptide: N-terminal (YQKLSYL; SEQ ID NO: 4), C-terminal (DFQYQLD; SEQ ID NO: 5) and central (LSYLDFQ; SEQ ID NO: 6). These peptides, labeled with a N-terminal biotin, were purchased from GenScript. The interaction between the shorter variants of G7 (SEQ ID NOs: 4-6) and GM-CSF was analyzed using ELISA test as described above. The results indicate that none of the short peptides binds to GM-CSF (FIG. 8A).

To determine the amino acid residues in the G7 peptide crucial for its activity, an alanine screening was performed, in which each of the residues in the peptide is substituted to alanine. To this end, 14 variants of G7 designated A1-A14 (SEQ ID NOs: 7-20, respectively) were generated, the sequences of which are presented in FIG. 8B and in Table 1. Whether elongation of the peptide by addition of the adjacent residues present in GM-CSR sequence (peptides W1 and W2, also termed A15 and A16, respectively; SEQ ID NO: 21 and 22, respectively) will affect the binding of G7 to GM-CSF was also tested. ELISA method was applied to test the activity of the aforementioned G7 variants. Peptides A2 and A11 (SEQ ID NOs: 8 and 17, respectively) exhibited higher binding capacity in comparison to G7, which was set to 100% (FIG. 8C). A8, A10-14 and W2 (also termed A16), corresponding to SEQ ID NOs: 14, 16-20 and 22, respectively, bound GM-CSF but not as strong as the unmodified peptide (FIG. 8C). Peptide W1 (also termed A15; SEQ ID NO: 21) showed very high affinity to the well surface as it bound to the control well without immobilized GM-CSF (FIG. 8C). The results indicate that amino acid residues 2, 11, 12 and 13 in G7 are not necessary for binding to GM-CSF. The influence of alanine substitutions in these positions on invasion of glioma cells induced by the presence of SV40 microglia cells was investigated by using Matrigel invasion test. The invasion of glioma cells in comparison to a positive control (Ctrl+) was reduced by 8 peptides: A2, A3, A5, A6, A9, A11, A12 and A13 corresponding to Sequence ID Nos.: 8, 9, 11, 12, 15, 17, 18 and 19, respectively (FIG. 8D). In line with the results of GM-CSF binding affinity, and as shown in FIG. 8D, variants A2 and A11-A13 (SEQ ID Nos: 8 and 17-19, respectively) exhibited the highest blocking activity, to similar levels as reported for the parental G7 peptide, confirming that substitutions in these residues did not significantly (FIG. 8D: **=p<0.01) affect G7 efficacy. Peptide A3 (SEQ ID NO: 9), which showed very weak binding to GM-CSF in the ELISA test (FIG. 8C) displayed also the weakest anti-cancer activity, yet, it reduced invasion by 40% which may suggest that even very weak binding of G7 peptide variant is sufficient for exerting G7's anti-invasion activity. Variants A1, A4 and A7 (SEQ ID Nos.: 7, 10 and 13, respectively) did not lower the number of invading cells in comparison to the positive control (Ctrl+; FIG. 8D). The results indicate that amino acid residues in positions 1, 4, 7, 10, 13 and 14 of G7 are important in G7—GM-CSF interaction and substitution of any of these residues in G7 peptide diminishes or reduce its activity.

Example 9: Anti-Tumor Activity of the G7 Peptide in Intracranial Gliomas

To verify the anti-tumor activity of G7 in vivo, fluorescently labeled U87 MG-RFP glioma cells (AntiCancer Inc.) were orthotopically implanted to Athymic Nude-Foxn1nu mice. G7 or G7S peptides (100 µM dissolved in cell culture medium) were injected along with transplanted glioma cells. Tumors were visualized 21 days post transplantation using in vivo fluorescence imaging system Xtreme Brucker (FIG. 10). After visualization animals were sacrificed, perfused with PBS and 4% paraformaldehyde (PFA). The brains were removed and post-fixed for 24 hours in fixative solution and placed in 30% sucrose in PBS at 4° C. Histological sections were prepared from frozen specimens. The brains were frozen using dry $CO_2$ and serial 20-µm-thick coronal sections were collected and stained with toluidine blue. Images were acquired using a Leica DM4000B microscope. The tumor areas were measured using Leica DM4000B software on every fourth brain slice and then tumor volumes were calculated. Tumor volumes in animals that received G7 were smaller than in controls or G7S receiving animals (FIG. 11).

Example 10: Solubility Study

G7 peptide is water insoluble and weakly soluble in aqueous buffers, such a PBS. Based on the data obtained for the various variants of G7 peptide (Example 8) several G7 variants were generated, where position that are less relevant for G7 activity were substituted or modified. Specifically, the new peptides were modified (relative to G7) by replacing amino acids in positions 2, 11 and 13 with lysine, or by adding lysine at the C or N terminus of G7, as shown in Table 2.

TABLE 2

| Pep-tide | Sequence | Seq. ID No. | Solubility [mg/ml] Water | PBS | Relative binding |
|---|---|---|---|---|---|
| G7 | YQKLSYLDFQYQLD | 1 | 0.00 | 0.12 | 100 |
| G7K-1 | KYQKLSYLDFQYQLD | 32 | 0.38 | 0.06 | 95 |

TABLE 2-continued

| Pep-tide | Sequence | Seq. ID No. | Solubility [mg/ml] Water | PBS | Relative binding |
|---|---|---|---|---|---|
| G7K2 | YKKLSYLDFQYQLD | 33 | 0.78 | 0.24 | 2 |
| G7K11 | YQKLSYLDFQKQLD | 34 | 0.13 | 0.03 | 108 |
| G7K13 | YQKLSYLDFQYQKD | 35 | 0.36 | 0.08 | 108 |
| G7K15 | YQKLSYLDFQYQKDK | 36 | 0.18 | 0.08 | 60 |

The results indicate that all modifications increased solubility in water. Next, binding of the modified peptides to GM-CSF was measured, using ELISA. G7 variant with lysine in position 2 (G7K2; SEQ ID NO: 33) exhibited the highest solubility, however this modification reduced GM-CSF binding in comparison to G7 peptide (Table 2). G7K-1 (SEQ ID NO: 32) and G7K13 (SEQ ID NO: 35) which were modified by the addition of lysine at the N terminus or by replacing the amino acid in position 13 with lysine, respectively, exhibited improved water solubility and maintained excellent binding to GM-CSF (Table 2).

G7K-1 variant (SEQ ID NO: 32) also exhibited high anti-cancer activity in comparison to G7, as determined in a Matrigel assay (FIG. 12). As a control for G7K-1 peptide two inactive alanine variants, KA7 (KYQKLSYADFQYQLD; SEQ ID NO: 37) and KA47 with substitution to alanine at positions 4 and 7 (KYQKASYADFQYQLD; SEQ ID NO: 38). These peptides also had a lysine residue at the N terminus. The results indicate that G7K-1 variant (SEQ ID NO: 32) exhibits significant (FIG. 12: *=p, 0.05) improvement in solubility without compromising its activity.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. An isolated peptide for inhibiting GM-CSF activity, said peptide being of 10-20 amino acids and comprising an amino acid sequence selected from the group consisting of: an amino acid sequence set forth in SEQ ID NO: 1 or variants thereof, SEQ ID NO: 23, and SEQ ID NO: 24, wherein each of the variants of SEQ ID NO: 1 is selected from SEQ ID NO: 1 with substitution of amino acids in any one or more of positions 2, 3, 5, 6, 9 and 11-13 with alanine or lysine and with or without addition of lysine at the N-terminus of SEQ ID NO: 1.

2. The isolated peptide of claim 1, wherein said peptide comprises SEQ ID NO: 1 or the variants thereof.

3. The isolated peptide of claim 2, wherein said peptide is consisting of SEQ ID NO: 1 or the variants thereof.

4. The isolated peptide of claim 1, wherein said peptide comprises an amino acid sequence selected from the amino acid sequence set forth in SEQ ID NO: 1, SEQ ID NO: 8, SEQ ID NO: 9, SEQ ID NO: 11, SEQ ID NO: 12, SEQ ID NO: 15, SEQ ID NOs: 17-19, SEQ ID NO: 23, SEQ ID NO: 24, SEQ ID NO: 32 and SEQ ID NO: 35.

5. The isolated peptide of claim 2, comprising an amino acid sequence selected from SEQ ID NO: 1, SEQ ID NO: 8, SEQ ID NO: 9, SEQ ID NO: 11, SEQ ID NO: 12, SEQ ID NO: 15, SEQ ID NO: 17, SEQ ID NO: 18, SEQ ID NO: 19, SEQ ID NO: 32 and SEQ ID NO: 35.

6. The isolated peptide of claim 5, comprising an amino acid sequence selected from: SEQ ID NO: 1, SEQ ID NO: 8 and SEQ ID NOs: 17-19.

7. The isolated peptide of claim 4, consisting of an amino acid sequence selected from: SEQ ID NO: 1, SEQ ID NO: 8, SEQ ID NO: 9, SEQ ID NO: 11, SEQ ID NO: 12, SEQ ID NO: 15, SEQ ID NOs: 17-19, SEQ ID NO: 23, SEQ ID NO: 24, SEQ ID NO: 32 and SEQ ID NO: 35.

8. The isolated peptide of claim 5, consisting of an amino acid sequence selected from: SEQ ID NO: 1, SEQ ID NO: 8, SEQ ID NO: 9, SEQ ID NO: 11, SEQ ID NO: 12, SEQ ID NO: 15, SEQ ID NOs: 17-19, SEQ ID NO: 32 and SEQ ID NO: 35.

9. The isolated peptide of claim 6, consisting of an amino acid sequence selected from: SEQ ID NO: 1, SEQ ID NO: 8 and SEQ ID NOs: 17-19.

10. The isolated peptide of claim 1 wherein said peptide consists of the sequence set forth in SEQ ID NO: 23.

11. The isolated peptide of claim 1 wherein said peptide consists of the sequence set forth in SEQ ID NO: 24.

12. The isolated peptide of claim 1, wherein said peptide is fused to a peptide assisting transport through the blood brain barrier (BBB).

13. A pharmaceutical composition comprising the isolated peptide of claim 1 and a pharmaceutical acceptable carrier.

14. The pharmaceutical composition of claim 13 for inhibiting migration of tumor cells.

15. The pharmaceutical composition of claim 14 wherein the tumor is glioma.

16. The pharmaceutical composition of claim 13 for the treatment of glioma.

17. The pharmaceutical composition of claim 14, wherein said glioma is selected from the group consisting of: ependymoma, astrocytoma, oligodendroglioma, glioblastoma, or a mixed glioma.

18. A method of treating glioma comprising administering to a subject in need thereof a therapeutically effective amount of a pharmaceutical composition comprising a peptide in accordance with claim 1.

19. The method of claim 18, wherein the peptide comprises the sequence set forth in SEQ ID NO: 1, or the variants thereof.

20. The method of claim 18, wherein treating glioma comprises inhibiting migration of tumor cells from the tumor to the cerebrospinal fluid.

21. The isolated peptide of claim 1, comprising the amino acid sequence of SEQ ID NO: 1 with an added lysine residue at the N-terminus of SEQ ID NO: 1.

* * * * *